US009022973B2

(12) United States Patent
Sexton et al.

(10) Patent No.: US 9,022,973 B2
(45) Date of Patent: May 5, 2015

(54) INTEGRATED INTRA-DERMAL DELIVERY, DIAGNOSTIC AND COMMUNICATION SYSTEM

(75) Inventors: Frederick A. Sexton, Rumson, NJ (US); Ian Ivar Suni, Potsdam, NY (US); Cetin Cetinkaya, Potsdam, NY (US); Stephanie Schuckers, Canton, NY (US); Eduard Sazonov, Potsdam, NY (US)

(73) Assignee: New World Pharmaceuticals, LLC, Charleston, SC (US)

(*) Notice: Subject to any disclaimer, the term of this patent is extended or adjusted under 35 U.S.C. 154(b) by 412 days.

(21) Appl. No.: 12/337,417

(22) Filed: Dec. 17, 2008

(65) Prior Publication Data

US 2009/0187167 A1 Jul. 23, 2009

Related U.S. Application Data

(60) Provisional application No. 61/014,184, filed on Dec. 17, 2007, provisional application No. 61/023,972, filed on Jan. 28, 2008.

(51) Int. Cl.
*A61M 31/00* (2006.01)
*A61B 17/20* (2006.01)
*A61M 37/00* (2006.01)

(52) U.S. Cl.
CPC ...... *A61B 17/205* (2013.01); *A61M 2037/0023* (2013.01); *A61M 2037/0038* (2013.01); *A61M 37/0015* (2013.01); *A61M 2037/003* (2013.01); *A61M 2037/0061* (2013.01)

(58) Field of Classification Search
CPC ............... A61M 2037/0023; A61M 2037/003; A61M 2037/0038
USPC ........... 604/65–67, 288.01–288.04, 502–505, 604/890.1, 891.1, 257, 258, 272; 600/583
See application file for complete search history.

(56) References Cited

U.S. PATENT DOCUMENTS 4,929,442 A 5/1990 Powell
4,983,377 A 1/1991 Murphy et al.
(Continued)

FOREIGN PATENT DOCUMENTS

JP 2005-503194 2/2005
JP 2005-507713 3/2005
(Continued)

*Primary Examiner* — Bhisma Mehta
*Assistant Examiner* — Larry R Wilson
(74) *Attorney, Agent, or Firm* — Leason Ellis LLP

(57) ABSTRACT

In one embodiment, an IDDC system utilizes an intelligent therapeutic agent delivery system comprised of one, but more likely an array of "cells" containing therapeutic agent(s) and/or diagnostic agents(s); an integrated bio-sensing system designed to sample and analyze biological materials using multiple sensors that include both hardware and software components. The software component involves biomedical signal processing to analyze complex liquid mixtures and a microcontrollers) acts as interface to the biosensors, to the therapeutic delivery elements, and to a communications system(s) for the purpose of controlling the amount of therapeutic agent to deliver and also to provide information in a useful form to interested parties on the progress of therapy and compliance thereto. The synergistic effect of combining the above describe elements is expected to dramatically improve patient compliance with prescribed therapy, quality and timeliness of care provided by physicians, and at the same time reduce the cost of providing effective healthcare to IDDC system users, thereby improving profitability for Managed Care organizations and pharmaceutical companies utilizing the system.

23 Claims, 17 Drawing Sheets

(56) References Cited

U.S. PATENT DOCUMENTS

| | | | |
|---|---|---|---|
| 5,315,995 A * | 5/1994 | Rivers | 600/342 |
| 5,356,785 A | 10/1994 | McMahon et al. | |
| 5,547,467 A | 8/1996 | Pliquett et al. | |
| 5,667,487 A | 9/1997 | Henley | |
| 5,667,491 A | 9/1997 | Pliquett et al. | |
| 5,736,154 A | 4/1998 | Fuisz | |
| 5,814,599 A | 9/1998 | Mitragotri et al. | |
| 5,860,957 A | 1/1999 | Jacobsen et al. | |
| 5,911,223 A | 6/1999 | Weaver et al. | |
| 5,983,135 A | 11/1999 | Avrahami | |
| 5,994,357 A | 11/1999 | Theoharides | |
| 6,002,961 A | 12/1999 | Mitragotri et al. | |
| 6,018,678 A | 1/2000 | Mitragotri et al. | |
| 6,050,988 A | 4/2000 | Zuck | |
| 6,165,458 A | 12/2000 | Foldvari et al. | |
| 6,175,752 B1 | 1/2001 | Say et al. | |
| 6,183,434 B1 | 2/2001 | Eppstein | |
| 6,190,315 B1 | 2/2001 | Kost et al. | |
| 6,256,533 B1 | 7/2001 | Yuzhakov et al. | |
| 6,334,856 B1 | 1/2002 | Allen et al. | |
| 6,379,324 B1 | 4/2002 | Gartstein et al. | |
| 6,444,200 B2 | 9/2002 | Foldvari et al. | |
| 6,503,231 B1 | 1/2003 | Prausnitz et al. | |
| 6,553,255 B1 | 4/2003 | Miller et al. | |
| 6,558,320 B1 | 5/2003 | Causey, III et al. | |
| 6,558,361 B1 * | 5/2003 | Yeshurun | 604/272 |
| 6,577,899 B2 | 6/2003 | Lebel et al. | |
| 6,611,707 B1 | 8/2003 | Prausnitz et al. | |
| 6,656,499 B1 | 12/2003 | Foldvari et al. | |
| 6,659,982 B2 | 12/2003 | Douglas | |
| 6,678,556 B1 * | 1/2004 | Nolan et al. | 604/21 |
| 6,692,456 B1 | 2/2004 | Eppstein | |
| 6,743,211 B1 | 6/2004 | Prausnitz et al. | |
| 6,767,341 B2 * | 7/2004 | Cho | 604/272 |
| 6,815,217 B2 | 11/2004 | Karl et al. | |
| 6,980,855 B2 | 12/2005 | Cho | |
| 7,044,911 B2 | 5/2006 | Drinan et al. | |
| 7,127,284 B2 | 10/2006 | Seward | |
| 7,141,034 B2 | 11/2006 | Eppstein et al. | |
| 7,226,439 B2 | 6/2007 | Prausnitz et al. | |
| 7,241,418 B2 | 7/2007 | Schaffler et al. | |
| 7,241,628 B2 | 7/2007 | Schaffler et al. | |
| 7,258,805 B2 | 8/2007 | Stemme et al. | |
| 7,262,068 B2 | 8/2007 | Roy et al. | |
| 7,273,458 B2 | 9/2007 | Prausnitz et al. | |
| 7,291,497 B2 | 11/2007 | Holmes et al. | |
| 7,344,499 B1 | 3/2008 | Prausnitz et al. | |
| 7,383,084 B2 | 6/2008 | Stern et al. | |
| 7,395,111 B2 | 7/2008 | Levin et al. | |
| 7,429,258 B2 * | 9/2008 | Angel et al. | 604/173 |
| 2001/0016683 A1 | 8/2001 | Darrow et al. | |
| 2002/0010412 A1 | 1/2002 | Eppstein | |
| 2002/0082543 A1 | 6/2002 | Park et al. | |
| 2002/0138049 A1 | 9/2002 | Allen et al. | |
| 2003/0083645 A1 | 5/2003 | Angel et al. | |
| 2003/0153900 A1 | 8/2003 | Aceti et al. | |
| 2003/0187338 A1 | 10/2003 | Say et al. | |
| 2003/0208167 A1 | 11/2003 | Prausnitz et al. | |
| 2003/0225360 A1 | 12/2003 | Eppstein et al. | |
| 2004/0039343 A1 | 2/2004 | Eppstein et al. | |
| 2004/0077995 A1 | 4/2004 | Ferek-Petric et al. | |
| 2004/0171921 A1 | 9/2004 | Say et al. | |
| 2004/0171980 A1 | 9/2004 | Mitragotri et al. | |
| 2005/0137525 A1 | 6/2005 | Wang et al. | |
| 2005/0137531 A1 | 6/2005 | Prausnitz et al. | |
| 2005/0148882 A1 | 7/2005 | Banet et al. | |
| 2005/0192557 A1 | 9/2005 | Brauker et al. | |
| 2005/0209565 A1 | 9/2005 | Yuzhakov et al. | |
| 2005/0228299 A1 | 10/2005 | Banet | |
| 2005/0228300 A1 | 10/2005 | Jaime et al. | |
| 2005/0261594 A1 | 11/2005 | Banet | |
| 2006/0064037 A1 | 3/2006 | Shalon et al. | |
| 2006/0189863 A1 | 8/2006 | Peyser et al. | |
| 2006/0195029 A1 | 8/2006 | Shults et al. | |
| 2006/0253005 A1 | 11/2006 | Drinan et al. | |
| 2007/0060800 A1 | 3/2007 | Drinan et al. | |
| 2007/0100222 A1 | 5/2007 | Mastrototaro et al. | |
| 2007/0129621 A1 | 6/2007 | Kellogg et al. | |
| 2007/0149873 A1 | 6/2007 | Say et al. | |
| 2007/0179372 A1 | 8/2007 | Say et al. | |
| 2007/0219597 A1 | 9/2007 | Kamen et al. | |
| 2007/0225676 A1 | 9/2007 | Prausnitz et al. | |
| 2007/0276318 A1 | 11/2007 | Henley | |
| 2008/0008745 A1 | 1/2008 | Stinchcomb et al. | |
| 2008/0009766 A1 | 1/2008 | Holmes et al. | |
| 2008/0027384 A1 | 1/2008 | Wang et al. | |
| 2008/0045879 A1 | 2/2008 | Prausnitz et al. | |
| 2008/0064626 A1 | 3/2008 | Zanella | |
| 2008/0077375 A1 | 3/2008 | Fernandez | |
| 2008/0124383 A1 | 5/2008 | Zanella | |

FOREIGN PATENT DOCUMENTS

| | | |
|---|---|---|
| JP | 2005-525141 | 8/2005 |
| WO | WO 99/02208 | 1/1999 |
| WO | WO 02/100474 | 12/2002 |
| WO | WO 03/037403 | 5/2003 |
| WO | WO 03/037404 | 5/2003 |
| WO | 2005/025413 | 3/2005 |

* cited by examiner

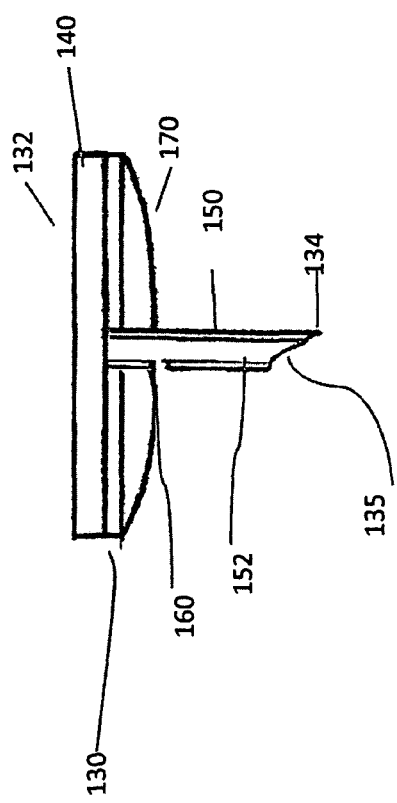
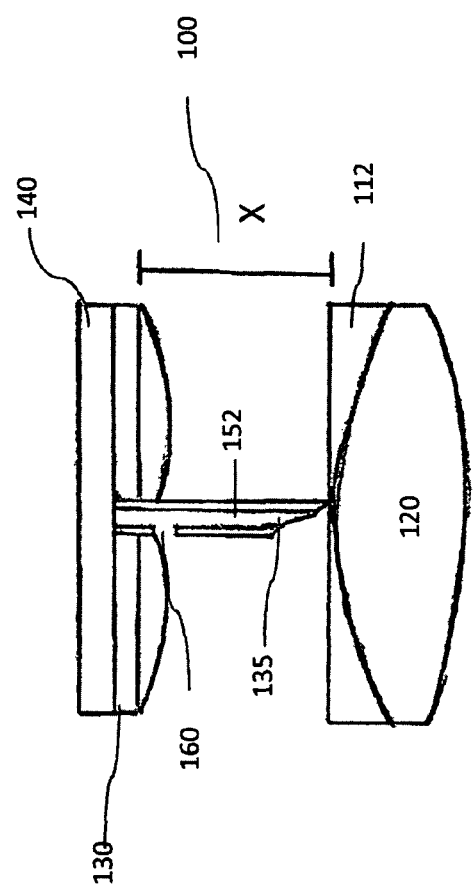
FIG. 2
FIG. 3

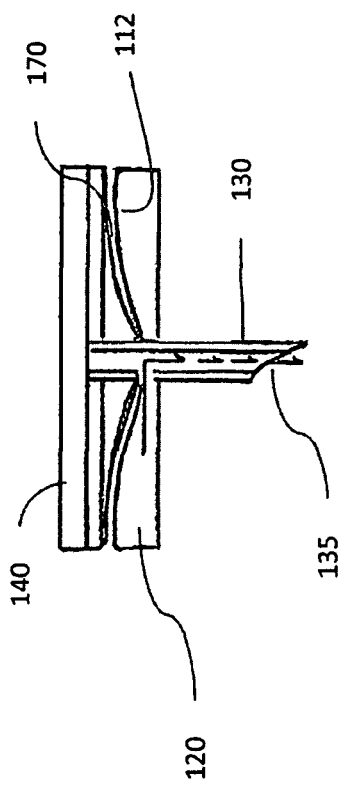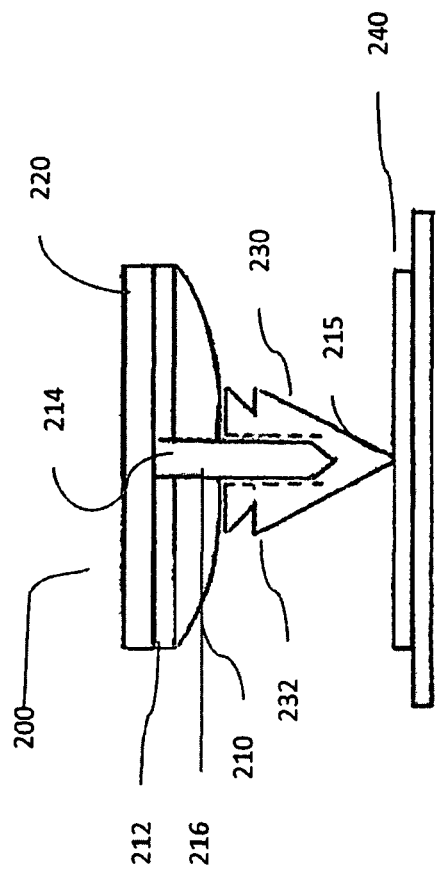

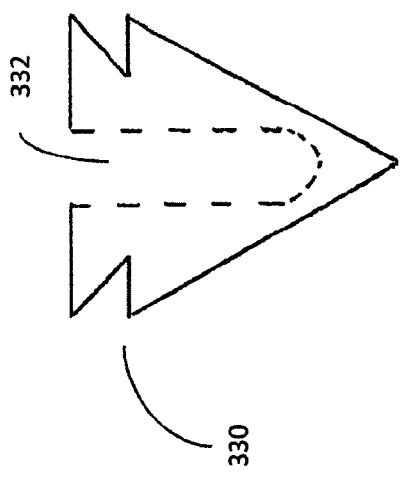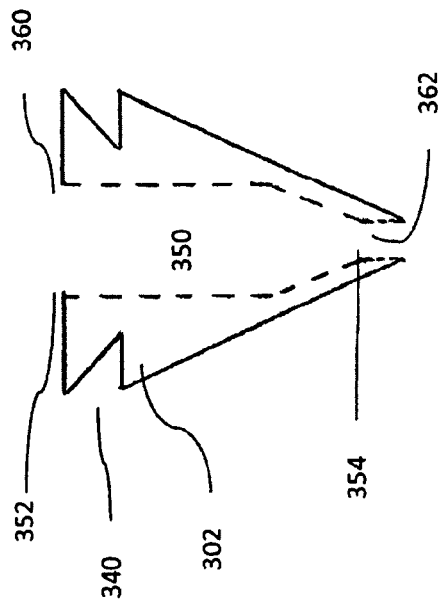

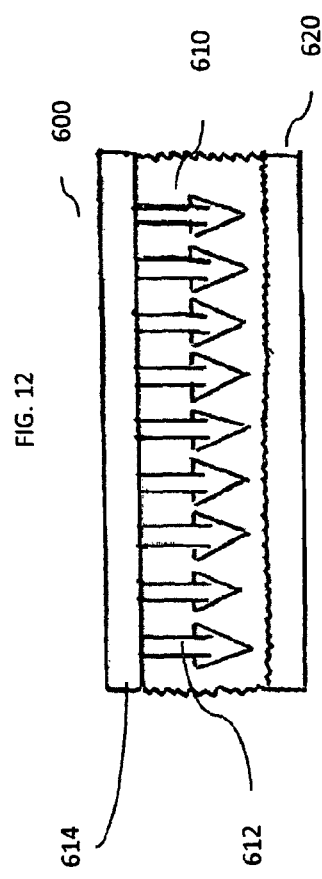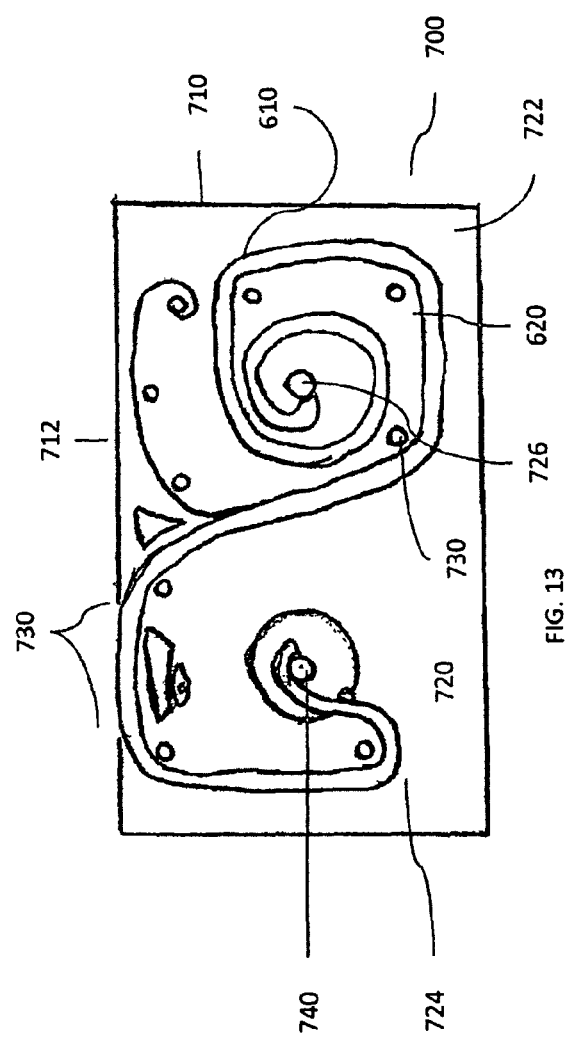

INTEGRATED INTRA-DERMAL DELIVERY, DIAGNOSTIC AND COMMUNICATION SYSTEM

CROSS REFERENCE TO RELATED APPLICATIONS

The present application claims the benefit of U.S. patent application Nos. 61/014,184 and 61/023,972, each of which is hereby expressly incorporated by reference in its entirety.

TECHNICAL FIELD

The present invention relates generally to an integrated intra-dermal delivery, diagnostic and patient interface system and in particular, relates to a transdermal delivery system having micro/nano features suitable for delivery below the stratum corneum layer, to an integrated biosensing system that can be used with the transdermal delivery system, an integrated micro-controller and an integrated communication system.

BACKGROUND

The healthcare industry in the U.S. drives an annual health related spending of approximately $2 trillion. Goods and services are provided by manufacturers of drugs, medical devices, and other supplies, with combined revenue of $300 billion, and by care providers—doctors, hospitals, clinics, nursing homes, etc., with combined annual revenue of $1.5 trillion. Most of the costs for healthcare is funded by private health insurers and government health insurance programs such as Medicare and Medicaid, with the private sector funding approximately $700 billion annually and the government providing combined annual payments of $1 trillion. Of the $1.5 trillion care provider market, the Managed Healthcare segment makes up approximately $350 billion.

This segment of the industry provides various types of health insurance plans designed with means of controlling the cost of healthcare related spending. The major products include health maintenance organizations (HMO's), preferred provider organizations (PPO's), point of services plans, and indemnity benefit plans.

The industry has expanded over the last decade on the premise that the traditional way of delivering healthcare was financially wasteful. Managed care companies attempt to control costs in four ways: by providing financial incentives to providers and users to minimize the amount of care used, contracting for services at discounted rates, reviewing expenses to determine the legitimacy of costs, and establishing low-cost treatment protocols providers are expected to follow. They are in effect, administrative intermediaries between healthcare providers and users.

In addition to using financial incentives to limit unnecessary medical care, managed healthcare companies use "utilization management" to review and standardize care. Committees of doctors and administrators review the actual services used in the network to determine if they're being used appropriately, and to recommend standards of care that doctors and hospitals are expected to follow. Committees also determine drug formularies that specify which drugs should be used to treat specific conditions. The statistical information collected for utilization management is also used for risk management and underwriting, the process of determining what payments to offer providers and what premiums to charge consumers. Computerized information and communications systems are vital to managed healthcare companies to process claims and manage records, and for statistical collection and analysis.

What appears to be an underdeveloped set of opportunities is preventive care and healing process management. According to PricewaterhouseCoopers, preventative care and disease management programs have untapped potential to enhance health status and reduce costs, a win for managed care and for the consumer.

Delivering care involves complex inter-relationships among multidisciplinary providers of various services and products. Opportunities for waste are rife. HealthCast 2020 survey respondents said sustainability depends on incentivizing clinicians, hospitals, pharmaceutical companies and payers to integrate care and manage chronic conditions together. The present applicant believes there is another critical component in this complex set of relationships, the patient. Wellness, prevention, and treatment regime compliance ultimately begins and ends with the patient. Patients are notoriously ineffective in maintaining compliance with their treatment regimes. Effectively integrating delivery, diagnostics, and communication into a single patient friendly system is expected to dramatically improve patient treatment outcomes and at the same time reduce cost and improve profitability for healthcare providers.

The pharmaceutical dosage form that may best be utilized to achieve the above described integration of functionality and technology is a patch or transdermal system. The currently available patch and transdermal technologies do not possess these capabilities and there is thus a need for an improved product that addresses and overcomes these deficiencies.

A transdermal drug delivery system is a system that delivers a dose of medication through the skin, for either local or systemic distribution. Often this promotes healing to a specific injured area of the body. An advantage of a transdermal drug delivery system over other types of drug delivery systems, such as oral, topical, etc., is that is provides a controlled release of the medicament into the patient. A wide variety of pharmaceuticals can be delivered via a transdermal drug delivery system.

One commonly found transdermal drug delivery system is a transdermal patch. A typical transdermal patch includes the following components: (1) a liner that protects the patch during storage and is removed prior to use; (2) a drug solution in direct contact with the release liner; (3) an adhesive that serves to adhere the components of the patch together along with adhering the patch to the skin; (4) a membrane that controls the release of the drug from the reservoir and multi-layer patches; and (5) a backing that protects the patch from the outer environment.

There are at least four different types of transdermal patches. One type is a single-layer drug-in adhesive where the adhesive layer of this system also contains the drug. The adhesive layer is surrounded by a temporary liner and a backing. A second type is a multi layer drug-in adhesive in which both adhesive layers are also responsible for the releasing of the drug; however, in this system, another layer of drug-in-adhesive is added. This path also has a temporary liner-layer and a permanent backing. A third type of path is a reservoir type that has a separate drug layer that is a liquid or semi-solid compartment containing a drug solution or suspension separated by the adhesive layer. A fourth type of patch is a matrix system that has a drug layer of a semisolid matrix containing a drug solution or suspension. An adhesive layer surrounds the drug layer partially overlaying it.

The limitations of these passive systems is that they are typically only effective in delivering (i) low molecular weight (<500 Da) compounds, (ii) lipophilic compounds, and (iii) potent compounds requiring low dosage (20-25 mg).

SUMMARY

According to one embodiment of the present invention, an intra-dermal delivery, diagnostic and communication (IDDC) system utilizes an intelligent therapeutic agent delivery system that includes at least one but more likely an array of "cells" containing therapeutic agent(s) and/or diagnostic agents(s). The IDDC system also includes an integrated biosensing system that is designed to sample and analyze biological materials to measure or determine a number of parameters including but not limited to i) clinical or therapeutic markers or surrogates thereof, e.g. blood pressure, blood or interstitial glucose level, histamine levels, cholesterol level, triglyceride level, etc., ii) circulating levels of therapeutic agent(s) using multiple sensors that include both hardware and software components, where the software component involves biomedical signal processing and/or pattern recognition to analyze complex liquid mixtures, etc. The IDDC system also includes at least one microcontroller to act as an interface to the biosensors, to the therapeutic delivery elements, and to the communications system(s) for the purpose of controlling the amount of therapeutic agent to deliver and also to provide information in a useful form to interested parties (patient, physicians, Managed Care Organization) on the progress of therapy and compliance thereto.

A communication system can be provided to manage the collection, storage and transmission of information from the above systems to a receiver system which may include ubiquitous communication devices, such as cell phones, PDA's, and infrastructure services such as WiFi, WiMax, cell towers, etc., with another role of the communication system(s) being initial configuration or ongoing modification of therapeutic agent delivery regimen (maximal dosage per unit of time, etc.). An energy storage and delivery subsystem(s) are included as part of the IDDC system for the purpose of providing other subsystems of the device with electric power which is stored in a battery, capacitor, transmitted through a communications link, including but not limited to a wireless link, an RF (radio frequency) link or by a combination of the above. The synergistic effect of combining the above described elements dramatically improves the potential for patient compliance with prescribed therapy, quality and timeliness of care provided by physicians, and at the same time reduces the cost of providing effective healthcare to IDDC system users thereby improving profitability for Managed Care organizations and pharmaceutical companies utilizing the system.

In one embodiment, an intra-dermal delivery, diagnostic and communication (IDDC) system includes a micro/nano sized cell containing drug that has at least one drug, therapeutic agent, etc., stored within a membrane of the cell. The cell also has a magnetic element associated therewith. The system also includes a drug delivery device in the form of a micro/nano lancet that has a drug delivery conduit defined by an entrance and an exit defined at a sharp distal end of the lancet. The lancet also has actuator, such as a magnetic or piezoelectric element associated therewith. At least one of the magnetic or piezoelectric elements is an element that is energized by a source of power. By energizing the electromagnetic or piezoelectric element, the lancet is driven toward and through drug containing cell so as to cause the drug or therapeutic agent in the membrane to flow into the inlet, through the lancet to the exit where it is discharged into the patient's body below the stratum corneum. Upon de-energizing the magnetic elements or piezoelectric elements after successful delivery of the drug or agent, the lancet can be removed. Alternatively, the electromagnetic or piezoelectric element can be energized with reverse polarity to retract the lancet.

In another embodiment, a micro/nano implant device includes a body that has a holding post and a magnetic or piezoelectric element. A micro/nano barbed implant that has the drug or agent incorporated therein is held at one end of the holding post (opposite the magnetic element). A magnetic membrane is positioned along the patient's skin and upon energizing the magnetic or piezoelectric elements, the barbed implant and holding post penetrate the stratum corneum and the implant is positioned at a desired depth below the skin. Upon de-energizing the magnetic or piezoelectric elements, the device can be withdrawn from the stratum corneum; however, the barbs of the implant engage the skin layer and thereby hold the implant in place at the desired location and depth below the patient's skin.

In still another embodiment, a micro/nano implant device includes a body that has a holding post supported by a first side of a substrate. A micro/nano barbed implant that has the drug or agent incorporated therein is held at one end of the holding post (opposite the substrate). The barbs are recessed or otherwise contained in a surrounding pliable material. The substrate is placed on the user's skin, with the barbs and pliable material facing the skin. A pressure applied to an opposite, second side of the substrate causes the pliable material to compress and permits the barbs to implant through the stratum corneum at a desired depth below the skin which is generally equal to the height of the barb off of the substrate. The barbs remain within the skin after the substrate is removed. The barbs are bio-absorbed over time. The pliable material may incorporate a skin contact layer including a topical anesthetic, which may be from but not limited to (benzocaine, butamben, dibucaine, lidocaine, oxybuprocaine, pramoxine, proparacaine (Alcaine), proxymetacaine, and tetracaine (AKA amethocaine.) the anesthetic being incorporated in a gel layer which may be comprised of cross-linked polymers or other materials, preferably something inert such as silica. The gel layer may have adhesion properties to ensure proper surface to skin contact and also allow for pain free removal as required.

In yet another embodiment, microneedles with channels are mounted on an oscillating movable base. The contact between a surface of the device and the skin is managed by and at the same time limited by a fixed casing. The microneedles are oscillated at a frequency between about 0 kHz to about 3 MHz (preferably between about 5 kHz to about 2 MHz), with amplitudes of between about 0 to about 1000 microns preferably between about 5 microns to about 250 microns). Amplitudes of oscillations are varied for drilling/opening channels in stratum corneum (SC)/epidermis/dermis and/or pumping/suction of drug/blood/interstitial fluids. The oscillating microneedles (with respect to the fixed device casting) create holes with specified properties in the stratum corneum. The design of the microneedles varies for specific requirements and depending upon the particular application. The back pressure and/or the SC-device interface pressure drive the drug to the target level in the intra-dermal space. Negative back pressure (difference) is utilized to extract blood and or interstitial fluid from the intra-dermal region into the appropriate reservoir(s) and in contact with (a) sensor(s). Pressure oscillations and motion control are utilized to move fluid in and out of the reservoir and in and out of contact with the sensor(s). The pressurized reservoirs utilize a synchronization scheme. Frequency and duty cycles as well as synchronization are optimized for the maximum performance. The biological sample can be obtained using any number of different techniques, including operating the device to draw the sample therein as when a pressure differential is created within the device.

Biosensing of the biological material may be accomplished utilizing electrical/electrochemical detection. The system can utilize one or more of i) application of DC voltage and measuring the DC current response (amperometry), ii) application of a DC current and measuring the DC voltage response (potentiometry), or iii) application of an AC voltage and measuring the AC current response (capacitance or impedance). In all cases, three electrodes are incorporated into the intra-dermal delivery, diagnostic and communication device, the working, reference and counter electrodes. These electrodes are positioned as closely together as possible, with analyte detection occurring at the working electrode. Ideally, the electrodes are designed such that the voltage is applied between the working and reference electrodes, while current is detected through the counter electrode.

A further embodiment involves the use of an electrode array, sometimes referred to as an "electronic tongue," to subtract out the signal from background or interfering species from those of the analyte(s) of interest. The electronic tongue includes hardware and software that will allow for accurate transdermal and or intra-dermal detection of an analyte in blood or in interstitial fluids. The hardware of an electronic tongue is an array of sensor electrodes at which distinct electrical/electrochemical signals are obtained. The individual electrodes are constructed from different materials, are coated with different membranes, or have different biomolecules immobilized at of near their surfaces. Each individual sensor electrode can employ amperometric, potentiometric, capacitance, or impedance detection, as described above. For an electronic tongue, reference electrodes may sometimes be shared by multiple working electrodes. The software of this type of system utilizes this array of electrodes to recognize patterns associated with an analyte of interest. By using an array of electrodes, a 'pattern' can be detected which is robust to selectivity issues with any one individual electrode.

For larger molecules that elicit an immune response, antibody electrodes can be used to construct an electrochemical immunosensor, which may also suffer from interference from other species beyond the analyte of interest. A number of U.S. patents, including U.S. Pat. Nos. 7,241,628; 7,241,418; 6,815,217; and 5,356,785 (each of which is hereby incorporated by reference in its entirety), describe methods to use reference channels to subtract out the effects of interfering species in antibody-, DNA-, and nucleic acid-based sensors; however, all of these methods suffer from interference arising from non-specific interactions and cross-reactivity and therefore have limitations and shortcomings.

Although these patents discuss the use of reference antibodies, nucleic acids, and DNA to subtract out the signals of interfering species, the patents discuss optical, not electrical/electrochemical methods, and none of the patents mentions intra-dermal or transdermal applications. The use of an ULSI sensor device allows more intricate methods for background subtraction, including an electronic tongue constructed from an array of electrochemical sensors.

The hardware of the electronic tongue also includes interfacing circuitry that allows interface between a microcontroller and individual sensors. The interfacing circuitry allows for individual reading of the signals from each of the sensors in the array, signal conditioning for shifting signal levels to ones interpretable by the microcontroller and digitization of the sensor signals for further processing by the software component.

The software component of an electronic tongue involves analyzing the collection of signals from this array of sensor electrodes by signal processing and pattern recognition algorithms. Pattern recognition methods are applied to the signals obtained by the sensor array for a large number of blood and/or interstitial fluid samples. This large data set is analyzed off-line to develop pattern recognition algorithms which recognize via the incorporated processor or transferred wirelessly to an external integrated processor to find patterns that allow subtraction of the signal from background or interfering species at each sensor electrode, allowing detection of only the species that each electrode is designed to detect. When antibodies or oxidoreductase enzymes are immobilized at or near a particular sensor electrode, that electrode will be designed to detect a specific, corresponding analyte. In general, the electronic tongue may also contain blank sensor electrodes that are present only for background subtraction through the use of pattern recognition algorithms.

In addition, pattern recognition can be performed via the incorporated processor or transferred wirelessly to an external integrated processor. Supervised pattern recognition algorithm, such as support vector machines, logistic regression, neural networks, may be utilized and include steps of preprocessing, feature extraction, and classification training. The large dataset is used to train the algorithm to recognize complex patterns. Sensing data is processed by an on-board electronic controller. Processed data and instructions are transmitted to/from the patient, physician and or a health care provider via the wireless communications.

The software component measures the quantity of interest (biomarker concentration) that is stored internally or reported via the communication subsystem, or establishes the presence of an event of interest (such as the above normal concentration of a certain biomarker) that may trigger delivery of a therapeutic agent or reporting of event detection via the communication subsystem. In the case of local processing and local delivery on the incorporated processor (microcontroller), the processor executes algorithms of the software component, establishes presence of an event of interest and delivers the therapeutic agent if necessary. In case of the remote processing by the software component of the biosensor data, the microcontroller receives the results through the wireless interface and then makes the delivery decision. Alternatively, the fact of detecting an event of interest is communicated to the user and the user makes a decision on therapeutic agent delivery communicated to the microcontroller via the wireless interface. The microcontroller initiates drug delivery by activating the delivery subsystem.

It will also be appreciated that microneedles with channels, microchannels, pumping units with controls, valves, pressure/motion actuators (acoustic, electric, etc.), reservoirs, dump sites (reservoirs), sensors (for biomarkers, etc.), ultrasound (low and high frequency), sonophoresis, vibration (flexural waves), thermal (thermophoretic, heat, burn, thermal oscillations, thermal skin/penetration), iontophoresis (electric field, polar molecule migration), electrical pulses (electromagnetic field), electroporation, magnetophoresis (magnetic field), and chemical permeation enhancers can be utilized.

Functionality is achieved when repeating pulsation of the needles creates a high pressure field in the holes of the stratum corneum for drug delivery either due to reservoir pressure and/or inertia/dynamic effects. For extraction of blood/interstitial fluids, the back-pressure is decreased. The reservoir pressure is oscillated and synchronized with the needle oscillations to increase the pumping action.

It will be appreciated that the systems and devices of the present invention as described herein can be used to deliver any number of different types (classes) of drugs. For example, the following drug classes and drugs are exemplary and can be incorporated into one or more devices and/or methods disclosed herein and in accordance with the present invention: cardiovascular agents and inotropic agents (e.g., cardiac glycosides); antiarrhythmic agents (e.g., quinidine); calcium channel blockers; vasodilators (e.g., nitrates and peripheral vasodilators); antiadrenergics/sympatholytics (e.g. beta-adrenergic blocking agents, alpha/beta-adrenergic blocking agents, antiadrenergic agents—centrally acting, antiadrenergic agents—peripherally acting, antiadrenergic agents—peripherally acting/alpha-1 adrenergic blockers); renin angiotensin system antagonists (e.g., angiotensin—converting enzyme inhibitors, angiotensin II receptor antagonists); antihypertensive combinations; agents for pheochromocytoma; agents for hypertensive emergencies; antihyperlipidemic agents (e.g., bile acid sequestrants, HGM-CoA reductase inhibitors, fibric acid derivatives); vasopressors used in shock; potassium removing resins; edentate disodium; cardioplegic solutions; agents for patent doctus arteriosus; sclerosing agents; endocrine/metabolic; sex hormones (e.g., estrogens, selective estrogen receptor modulator, progestins, contraceptive hormones, ovulation stimulants, gonadotrophins, including gonodotropin-releasing hormones, gonodotropin-releasing hormone antagonists, androgens, androgen hormone inhibitor, anabolic steroids); uterine-active agents (e.g., abortifacients, agents for cervical ripening); bisphosphonates; antidiabetic agents (e.g., insulin, insulin-high-potency, sulfonylureas, alpha-glucosidase inhibitors, biguanides, meglitinides, thiazolidinediones, antidiabetic combination products); glucose elevating agents; andrenocortical steroids (e.g., adrenal steroid inhibitors, corticotrophin, glucocorticoids, glucocorticosteroids/corticosteroid retention enemas, glucocorticosteroids/corticosteroid intrarectal foam, mineralocorticoids); thyroid drugs (e.g., thyroid hormones, antithyroid agents); growth hormone (e.g., posterior pituitary hormones, octreotide acetate); imiglucerase; calcitonin-salmon; imiglucerase; sodium phenylbutyrate; betaine anhydrous; cysteamine bitartrate; sodium benzoate/sodium phenylacetate; bromocriptine mesylate; cabergoline; agents for gout (e.g., uricosurics); antidotes (e.g., narcotic antagonists); respiratory agents; bronchodilators (e.g., sympathomimetics and diluents, xanthine derivatives, anticholinergics); leukotriene receptor antagonists; leukotriene formation inhibitors; respiratory inhalant products; corticosteroids; intranasal steroids; mucolytics; mast cell stabilizers; respiratory gases; nasal decongestants (e.g., arylalkylamines and imidazolines); respiratory enzymes; lung surfactants; antihistamines; alkylamines, non-selective; ethanolamines, non-selective; phenothiazine, non-selective; piperazine, non-selective; piperidines, non-selective; phthalazinone, peripherally-selective; piperazine, peripherally-selective; piperidines, peripherally-selective; antiasthmatic combinations; upper respiratory combinations; cough preparation; renal and genitourinary agents; interstitial cystitis agents.

Some suitable drugs that fall within the above classes include Rosiglitazone, Interferon α 2b, Omalizumab (Xolair), Cetirizine, Erythropoietin (EPO), and metoprolol tartrate. In generally, any number of different protein drugs can be delivered with the system of the present invention. In addition, the systems and devices of the present invention can use any number of different biomarkers depending upon the drug that is of interest. For example, some biomarkers of interest include but are not limited to glucose alanine, Hepatitis C virus, immunoglobulin E, histamine, ferritin, transferrin, and C-reactive protein. It will therefore be appreciated that the biomarker is selected in view of the drug that is selected for delivery or the disease selected for monitoring.

Moreover, the present invention offers significant improvements over conventional systems, including those that use an electronic tongue, where signal processing algorithms are applied to an array of electrodes to subtract out background or interfering signals. In particular, the conventional systems do not use antibodies immobilized on electrodes and further, the conventional systems do not use capacitance or impedance detection, both of which involve AC rather than DC signals.

The use of an "electronic nose", which is a similar concept to the electronic tongue described hereinbefore is known. However, the electronic nose is designed for detecting species in the gas phase. In accordance with the present invention, gas phase or at least airborne particulate detection can be incorporated in the present system in the event that the user wishes to manage a biological response and/or drug delivery using one of the devices described hereinbefore based on signals from the ambient environment. In this event, the signals would not originate from a liquid medium but instead would originate from a gaseous or atmospheric medium (e.g., an ambient signal that is from pollen in the atmosphere). The electrodes and electrical/electrochemical methods that are employed in this situation are selected and customized based on the location of origination of the ambient signal (e.g., gaseous or atmospheric medium).

BRIEF DESCRIPTION OF THE DRAWING FIGURES

The foregoing and other features of the present invention will be more readily apparent from the following detailed description and drawings figures of illustrative embodiments of the invention in which:

FIG. 2 is a side cross-sectional view of a micro/nano drug delivery device for use with the cell of FIG. 1;

FIG. 3 is side cross-sectional view of the drug delivery device proximate the cell prior to delivery of the drug;

FIG. 4 is a side cross-section view of the drug delivery device inserted into the patient's skin after piecing the cell to deliver the drug to the patient;

FIG. 5 is a side cross-sectional view of a micro/nano implant according to a transdermal delivery system according to another embodiment;

FIG. 7 is a side cross-sectional view of a micro/nano implant according to another embodiment;

FIG. 8 is a side cross-sectional view of a micro/nano implant according to yet another embodiment;

FIG. 12 is a side cross-sectional view of a micro/nano barb assembly with a protective gel coating;

FIG. 13 is a side cross-sectional view of an applicator for use with micro/nano drug delivery devices, including the one of FIG. 12;

Figure 19:
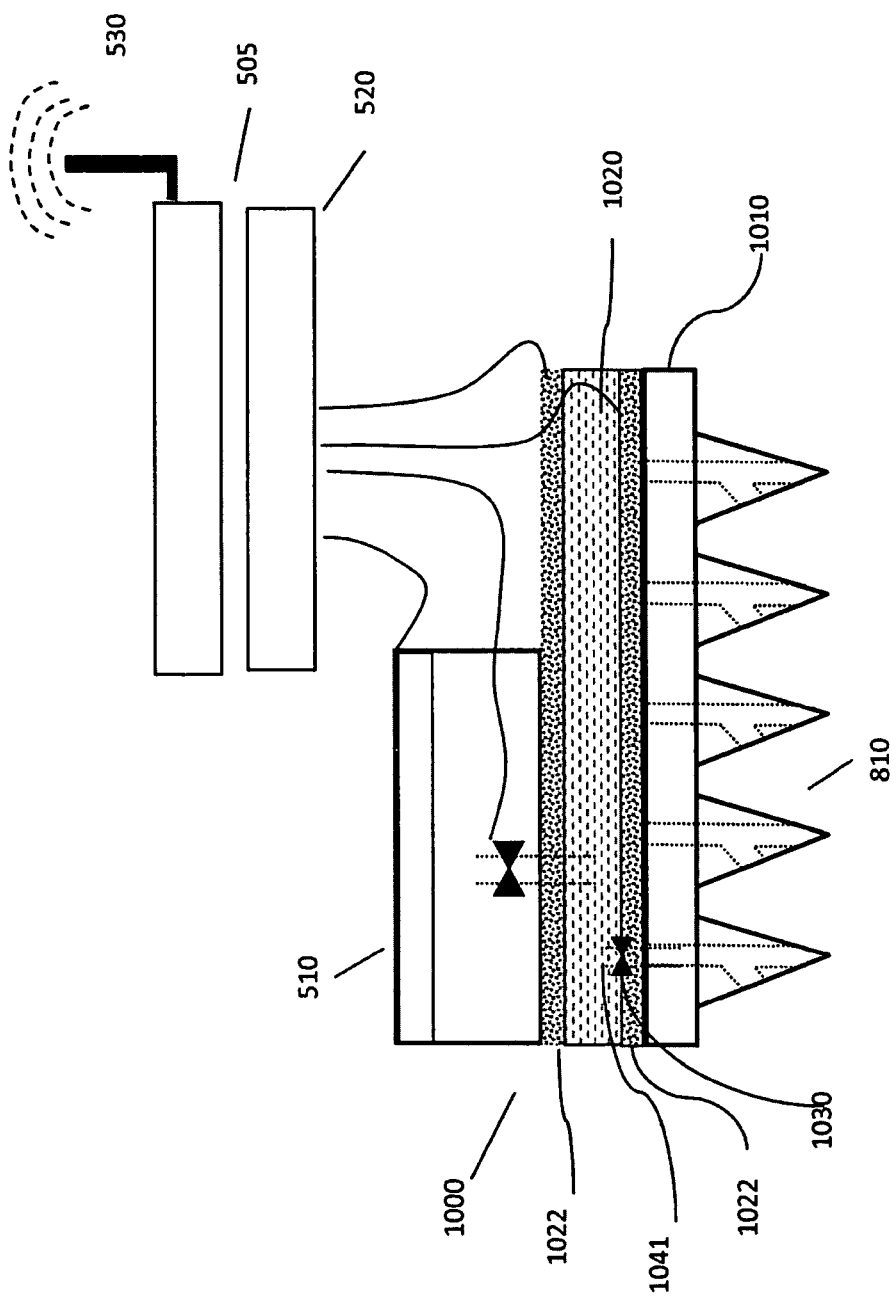
Figure 20:
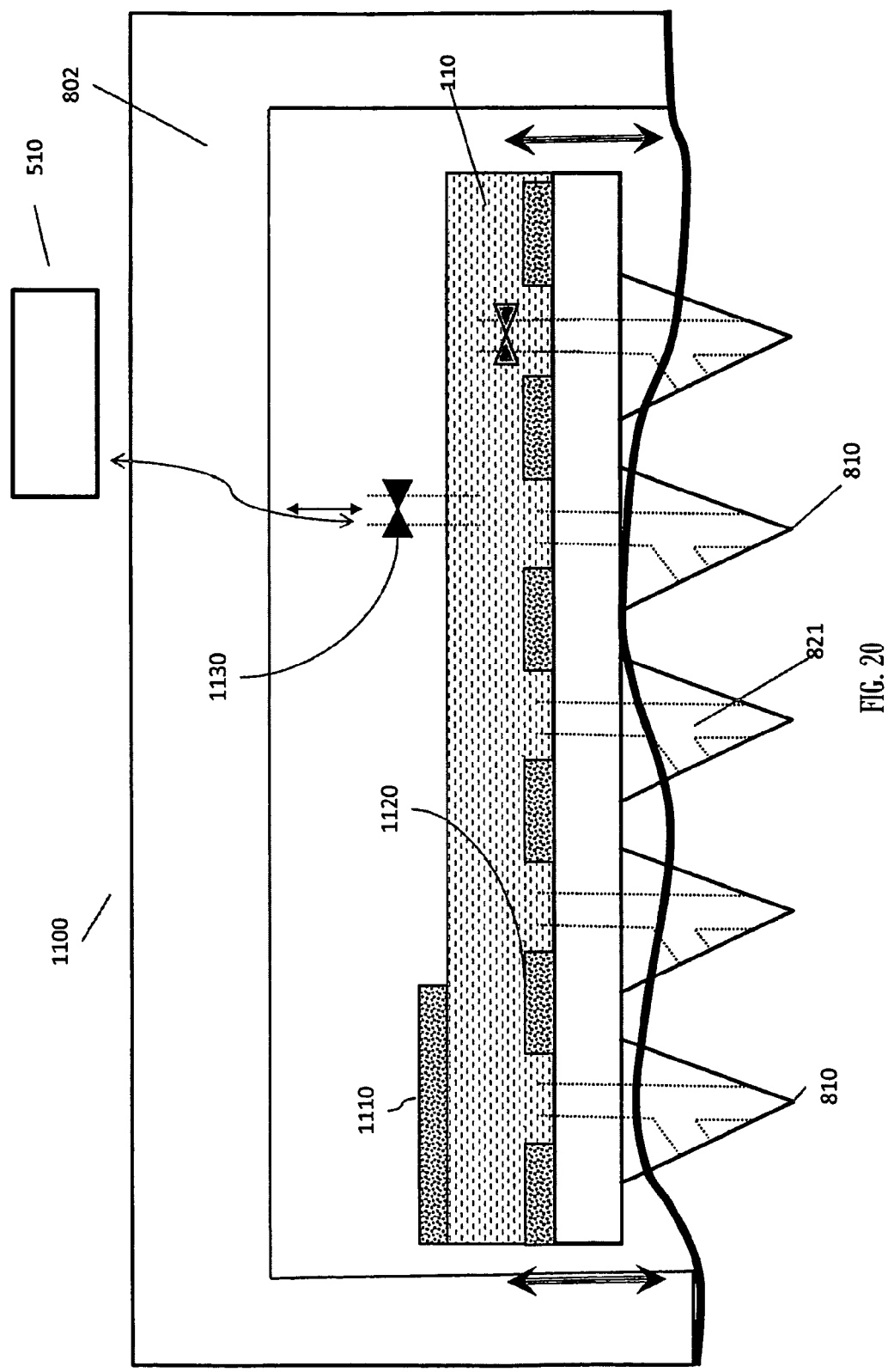
Figure 21:
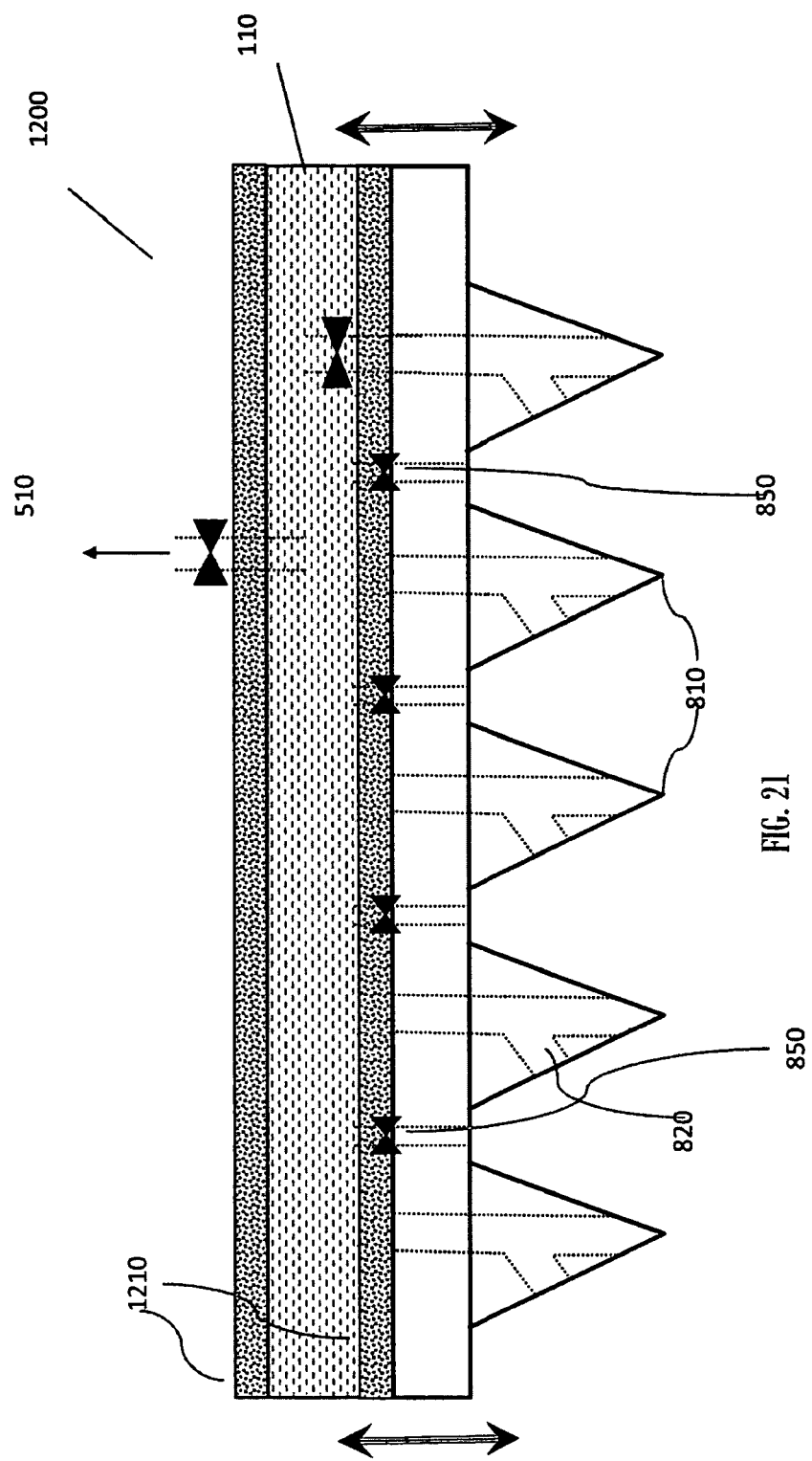
Figure 22:
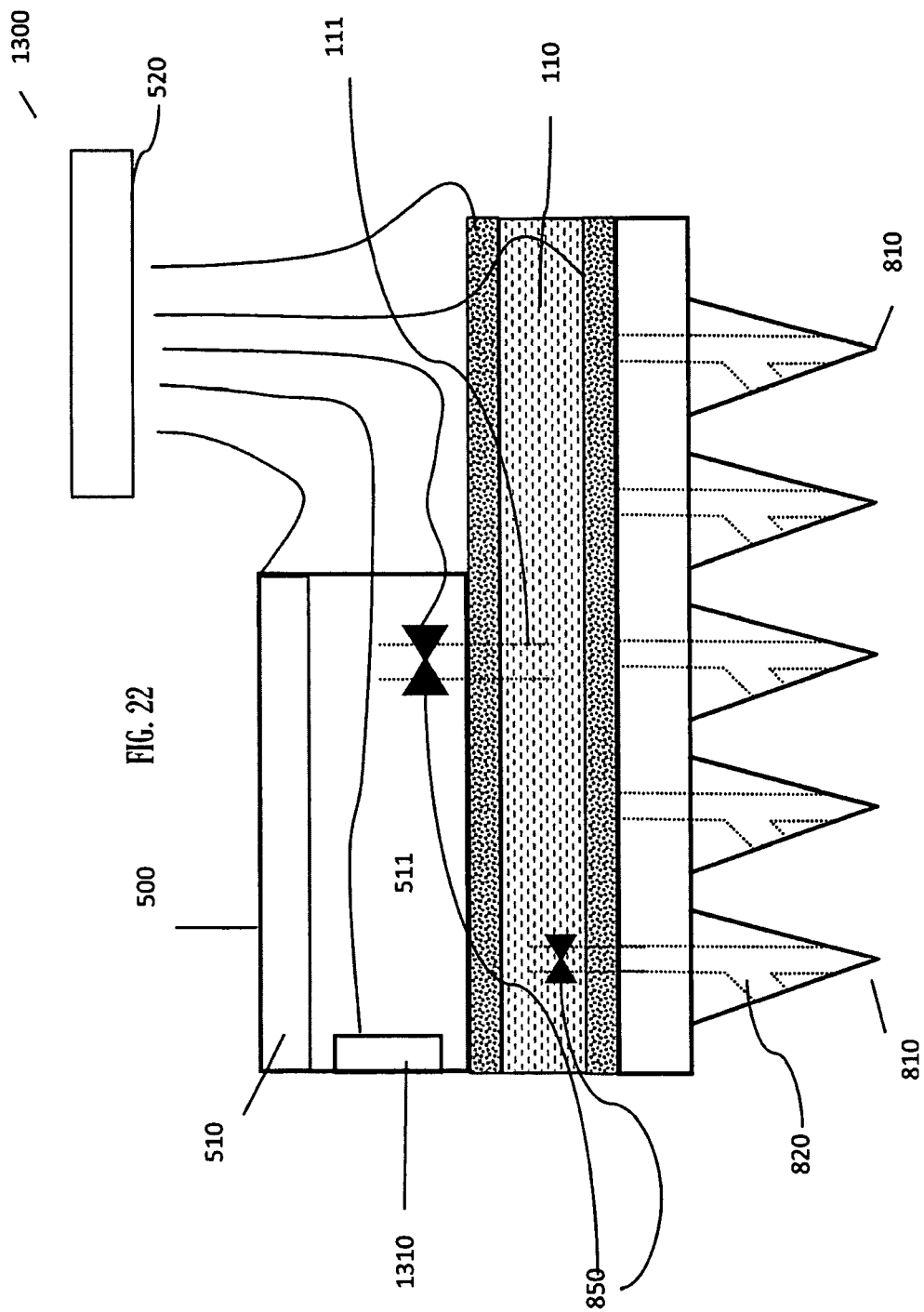

FIG. 19 schematic diagram of the drug delivery device interfaced with biosensors, control system hardware, and communication units;

FIG. 20 is a cross-sectional view of an alternate micro/nano drug delivery device depicting pressure and motion actuators;

FIG. 21 is a cross-sectional view of an alternate micro/nano drug delivery device depicting piezoelectric componentry; and FIG. 22 is a cross-sectional view of an alternate micro/nano drug delivery device depicting biosensor interface with drug delivery sub-unit and control system.

DETAILED DESCRIPTION OF PREFERRED EMBODIMENTS

An optimal transdermal delivery system, for some applicants, is a topical patch, gel, cream, or similarly applied system that is easily applied by a patient or caregiver onto a convenient, but unobvious location. It will deliver its target drug(s), which may be either small molecules or biologics, with a predictable and programmable rate and absorption kinetics. The system in one form can be designed to deliver drugs for local or regional effect. In other embodiments, the system can be designed to achieve the predictability of an i.v. infusion, but without the pain and inconvenience of having an installed port. The system should only produce a depot effect by design. In addition, the drug release kinetics should not be interrupted by normal use and should be difficult to intentionally disrupt. The duration and extent of delivery is controlled by a combination of release site, release rate, and surface area. It is an objective to provide controlled delivery from a single day application up to and including 10 days of therapy to accommodate most antibiotic prescription regimes. However, it will be appreciated and understood that the time period for use of the delivery systems described herein varies depending upon the condition to be treated. For example, the devices are intended for use as part of a chronic therapy and therefore, controlled delivery can be achieved for a single day through the end of a person's life depending upon the circumstances and the application. Thus, the time periods and length of treatment recited above is merely exemplary and not limiting.

In accordance with one embodiment of the present invention the above objectives are achieved by an intra-dermal delivery diagnostic and communication system 100 shown in FIGS. 1-4. The system 100 is of the type that includes one or more drug reservoirs or depots and includes a means for delivering the drug to a patient. The system 100 includes at least one drug containing member 110 that stores the drug that is to be delivered. The member 110 includes an actuator 112 that can be in the form of a magnetic membrane that is formed of a magnetic material and a drug containing cell 120 (other actuators can be used, such as a piezoelectric based actuator and therefore, the discussion herein of magnetic membrane 112 is intended to cover one embodiment and is not limiting of the invention since actuator 112 can be another type of actuator). The drug containing cell 120 is flexible but provides the necessary stability to provide a cell that contains the drug that can be in the form of a drug solution or suspension. The drug containing cell 120 thus defines an interior pocket or compartment that contains and stores the drug that is to be delivered. While, the term "drug" is used herein, it will be understood that other substances besides drugs can be stored in the cell. For example, the cell can contain therapeutic agents, vitamins, etc., and is not limited to a substance that is classified as a "drug" per applicable government guidelines.

Figure 1:
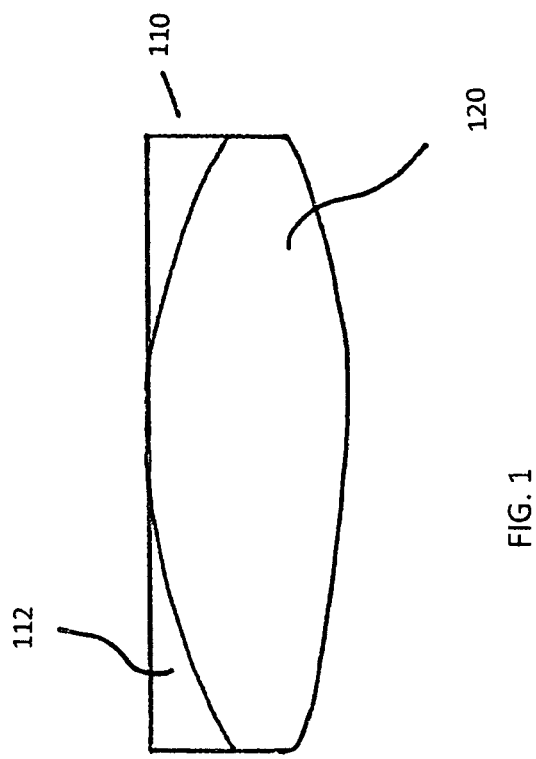
FIG. 1 is a side cross-sectional view of a micro/nano drug containing membrane or cell according to a transdermal delivery system according to one embodiment.

As illustrated in FIG. 1, the magnetic membrane 112 is disposed over the cell 120. The shape and size of the cell 110 can be tailored according to the given application, including the type of drug to be delivered and the quantity that is to be delivered over time.

The drug delivery system 100 also includes a drug delivery device 130 that is complementary to the drug containing member 110 and is designed to mate therewith for controlled delivery of the drug that is contained in the cell 120. For example, the drug delivery device 130 can be in the form of a mechanically robust micro or nano lancet or the like that acts as a carrier portal and cell sealing device. The lancet 130 includes a first end 132 and an opposing second end 134. At the first end 132, the lancet 130 has a magnetic contact 140. The magnetic contact 140 can be in the form of one or more pads or other type of structures. In the illustrated embodiment, the lancet 130 has a support structure 134 (planar surface) that supports the magnetic contact 140.

The lancet 130 also has an elongated hollow body 150 through which the drug is delivered as described below. The hollow body 150 can be an elongated tubular structure (cylindrically shaped tube) that has an inlet 160 (drug entrance or orifice) that is formed between the first and second ends 132, 134 and is located along one side of the hollow body 150. In other words, the hollow body 150 includes a main bore 152 and the inlet 160 is formed perpendicular to the main bore 152. The second end 134 represents an open end of the hollow body 150 and thus represents a distal opening 135 of the main bore 152. The distal opening 135 at end 134 serves as a drug delivering orifice or exit. It will be appreciated that the second end 134 of the lancet 130 is a sharpened end that permits the lancet to pierce an object, such as the skin of the patient. The second end 134 can thus be a sharp, beveled edge.

The lancet 130 also includes a biasing member 170 that is disposed between the hollow body 150 and the support structure 134. The biasing member 170 serves to move the lancet 130 relative to the drug containing member 110 after delivery of the drug from within the cell 120. In the illustrated embodiment, the biasing member 170 is in the form of a spring, such as a leaf spring, that is attached to an underside of the support structure 134 and bows outwardly toward and into contact with the hollow body 150 at a location proximately adjacent to the inlet 160 such that the biasing member 170 does not obstruct drug flow into the inlet 160.

The biasing member 170 will thus store energy when the structure is compressed as shown in FIG. 4 and as described below. In lieu of a biasing element, spaced electromagnets can be energized so as to attract and thereby compress an intervening space, and thereafter energized so as to repel and thereby restore the dimensions of the intervening space, if desired.

According to one embodiment and as shown in FIG. 3, the distance X is approximately equal to the stratum corneum, which is the outermost layer of the epidermis (the outermost layer of the skin). It is composed mostly of dead cells that lack nuclei. The thickness of the stratum corneum varies according to the amount of protection and/or grip required by a region of the body. For example, the hands are typically used to grasp objects, requiring the palms to be covered with a thick stratum corneum. Similarly, the sole of the foot is prone to injury, and so it is protected with a thick stratum corneum layer. In general, the stratum corneum contains 15 to 20 layers of dead cells.

The sequence of using the system 100 to administer one or more drugs to a patient in accordance with one method of the invention can be as follows. First, the proper drug containing member 110 is selected based on the needs of the patient and then it is arranged so that the drug containing cell 120 faces and is placed in contact with a target location of the patient's skin where the drug is to be administered. It will therefore be appreciated that the magnetic membrane 112 faces away from the patient's skin. The drug delivery device 130 is then positioned so that the second end 134 faces the magnetic membrane 112. In other words, the sharp, piercing end of the lancet 130 faces the drug containing member 110 as shown in FIG. 3 which is an illustration of the system just prior to administration of the drug to the patient.

Next, the magnetic elements, namely the magnetic membrane 112 and the magnetic contact 140 are energized using conventional techniques. For example, a microprocessor can include a circuit that is used to energize the magnetic membrane or other electric components (e.g., capacitors) can be used to energize the two magnetic elements. The energized magnetic elements 112, 140 close the gap therebetween resulting in the sharp second end 134 of the lancet 130 piercing first the magnetic membrane 112 and then piercing through both the top surface and the bottom surface of the cell or membrane 120. The magnetic elements 112, 140 are in contact with one another as shown in FIG. 4 and the second end 134 of the lancet 130 is located well below the bottom surface of the cell 120.

At least one of the magnetic elements is an electromagnet; the other can be a permanent magnet or permanent magnet layer. The magnet system is energized when there are two electromagnets that are being driven by an energizing signal, or when there is one electromagnet being driven by an energizing signal in proximity to a permanent magnet.

The construction of the lancet 130 permits the drug within the cell 120 to be delivered therethrough to the patient and more specifically, the dimensions of the lancet 130 and the cell 120 are selected so that when the magnetic elements 112, 140 are in contact with one another (FIG. 4), the drug inlet 160 is located within the cell 120 itself, thereby allows the drug contained therein to flow through the inlet 160 and into the main bore 152. The drug then flows along the arrows shown in FIG. 4 and flows from the inlet 160 down the main bore 152 toward and out of the outlet at the second end 134 and into the patient. As mentioned above, the length of the lancet 130 is selected so that the second end 134 is at a desired penetration depth.

Accordingly, the pressure from the lancet 130 on the drug containing member 110 forces the drug in the cell 120 to flow into the main bore 152 and into the target tissue.

Also, as the lancet 130 pierces the drug containing member 110, the biasing member 170, if provided, compresses and stores energy.

At least one of the magnetic elements 112, 140 can de-energize to allow the lancet 130 to be free and move relative to the drug containing member 110 and also to allow the biasing member 170 to release its energy and return to a relaxed state. This action results in the lancet 130 being withdrawn from the stratum corneum.

It will also be appreciated that the magnetic elements 110, 140 can be energized multiple times, e.g., in succession, and this will result in a pumping action to ensure that an optimal amount of the drug in the cell 120 is delivered to into the patient's skin.

The entire system 100 includes both macro and micro scale components. For example, the component of the system that is disposed within the body is constructed on a micro/nano scale so as to deliver the drug to the patient in an unobvious manner; however, in some embodiments, the structure in which the microscale components are incorporated, such as a path, are on a macroscale. When the system 100 is incorporated into a transdermal patch or the like, the means of adhering the system to the skin must be hypo-allergenic and substantially robust enough to withstand normal daily function including hygiene practice, athletic participation, sleeping, etc.

FIG. 5 shows an intra-dermal drug delivery system 200 according to another embodiment. The system 200 is similar to the system 100 in that it utilizes a similar lancet design to create a micro/nano implant that is delivered into the patient. In this embodiment, the system 200 includes an implant device 210 that includes a support structure having a base 212 at a first end 214 and an elongated holding post 216 that extends outwardly from an underside of the base 212. The base 212 can be in the form of a planar surface, with the holding post 216 being oriented perpendicular thereto. An implant device 210 is broadly speaking any type of device that can be implanted into a patient (e.g., a member that enables intra-dermal installation).

The system 200 also includes a magnetic element 220 which can be in the form of a magnetic strip that is coupled to the base 212. For example, the magnetic element can be a thin planar layer of magnetic material that seats on and is coupled to an upper surface of the base 212. The magnetic element 220 thus represents one end of the implant device 210.

Similar to the system 100, the implant device 210 can include a biasing member 170. In the illustrated embodiment, the biasing member 170 is in the form of a spring, such as a leaf spring, that is attached to an underside of the base 212 and bows outwardly toward and into contact with the holding post 216. Alternatively, a magnetic system arrangement can be used as described above to compress and restore dimensions of the system 200 before and after the implant is deposited in the skin.

The system 200 also includes a drug carrying component 230 which in this case is in the form of micro/nano implant body with a barbed structure 232. As illustrated in FIG. 5, implant body 230 is coupled to a second end 215 of the holding post 216. The implant body 230 has one or more barbs 232 and terminates in a sharp end 234 that is intended to pierce the patient's skin.

The system 200 further includes a magnetic membrane 240 that is intended for placement on the patient's skin. The magnetic membrane 240 can thus be a planar magnetic layer (strip) that can lie against the patient's skin at a target location where the drug is to be administered. In order to hold the magnetic membrane 240 in position on the patient's skin, the magnetic membrane 240 can includes an adhesive or the like, such as an adhesive border that serves to temporarily attach the magnetic membrane 240 to the skin.

It will be appreciated that in this design, the implant 230 is the member that carries the drug that is to be administered into the patient's body. The implant 230, including the barbs 232 can be formed of a number of different material, including a polymer matrix with biodegradable properties. In addition, the implant 230 should be imperceptible when in place and non hypo-allergenic and have a predictable disintegration where the disintegration rate controls the drug release rate since the drug is incorporated into the implant material. Alternatively, the implant 230 can be formed of a resorbable polymer matrix where the release rate is independent of resorption rate and resorption occurs after delivery of the drug content.

The system 200 is operated in the following manner to delivery the drug to the patient. First, the magnetic membrane 240 is placed on the patient's skin and the implant device 210 is positioned as shown in FIG. 5 with the implant 230 facing the magnetic membrane 240. The magnetic element 220 and the magnetic membrane 240 are energized to cause the magnetic elements 220, 240 to close the gap therebetween causing the device 210, including the holding post 216 and implant body 230, to penetrate the stratum corneum painlessly. The biasing member 170 compresses and stores energy.

When the magnetic elements 220, 240 are adjacent one another, the implant 230 has been delivered to the desired penetration depth. The magnetic elements 220, 240 are de-energized releasing the implant device 210 and allowing the biasing member 170 to release its stored energy and return to its relaxed position, thereby withdrawing the base 212 and holding post 216 from the stratum corneum. Upon this withdrawal action, the barbs 232 of the implant body 230 engages the skin layer resulting in only the holding post 216 to be withdrawn from the patient. This results in the implant body 230 being left behind at the desired location and at the desired depth. The dimensions of the implant body 230 and the dimensions and locations of the barbs 232 are selected to accomplish this and result in the implant body 230 and the drug therein to be left at the proper location within the patient's body.

Figure 6:
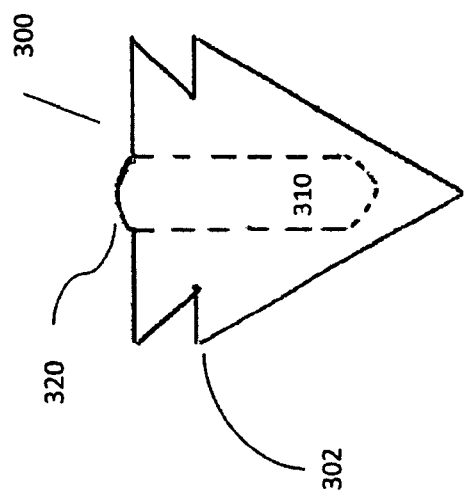
FIG. 6 is a side cross-sectional view of a micro/nano implant according to another embodiment.

FIG. 6 shows yet another embodiment for the barbed implant body and more specifically, an implant body 300 is shown for use with the system 200. The implant body 300 is similar to implant body 230 in that includes barbs 302; however, in this embodiment, the implant body 300 has a drug containing reservoir 310 formed therein. The reservoir 310 can be simply a bore formed therein that is open only at a first (top) end 304 of the implant body 300.

The implant body 300 and barbs 302 are fabricated out of a bioresorbable material that is formed to include the reservoir 310 that contains liquid, semi-solid or solid drug containing materials. The reservoir 310 is sealed with a sealing membrane 320 that extends across the open end 304 of the body 300 to seal the drug in place. The sealing membrane 320 can be formed of a material that penetrates or dissolves.

The release rate of the drug is controlled by the dissolution rate of payload (small or large molecules) and the surface area of the reservoir opening, as well as post membrane disruption/disintegration.

FIG. 7 shows an implant body 330 that is formed of a solid or porous matrix and includes a holding post cavity (bore) 332 for receiving the holding post 216 (FIG. 5). The release rate is controlled by disintegration/dissolution of the matrix in interstitial fluids.

The shape of the barb in any of the above embodiments can be anything that allows for imperceptible penetration and a sufficient rear side surface to prevent the barb from backing out of the skin.

FIG. 8 shows another embodiment in which an implant body 340 has a drug containing reservoir 350 formed therein. The reservoir 350 can be simply a bore formed therein that is open at both a first (top) end 352 of the implant body 340 and at or near a second end 354 of the implant body 340. The reservoir 350 is sealed with a first sealing membrane 360 that extends across the open first end 352 of the body 300 and with a second sealing membrane 362 that extends across the open second end 354 to seal the drug in place within the reservoir 350. The sealing membranes 360, 362 can be formed of a material that penetrates or dissolves.

Figure 9:
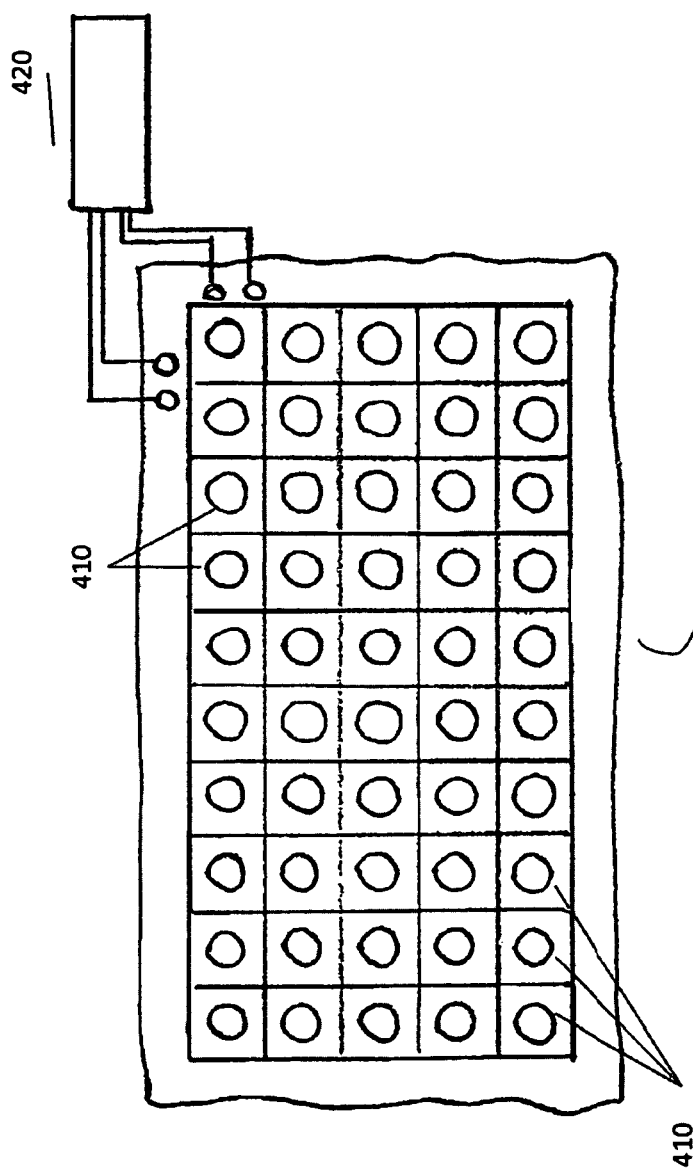
FIG. 9 is a top plan view of an array of micro/nano drug delivery devices that are part of a transdermal delivery system.

FIG. 9 illustrates a drug delivery system 400 that is in the form of an array of a plurality of drug delivery devices 410 that can be fired/triggered based on a prescribed time or response signal. For example, the system 400 can be linked to an energy source 420 that includes a time sequenced firing mechanism. In other words, each of the individual drug delivery devices 410 is linked to the energy source 420 and a controller (microprocessor) can be programmed depending upon the patient's needs to sequentially fire a prescribed number of the drug delivery devices 410 over a period of time to delivery the drug at set time intervals and over the period of time. It will also be appreciated that the array can include more than one drug in that some of the drug delivery devices 410 thereof can contain one drug, while others contain other drugs. By linking each drug delivery device 410 to the energy source, different drugs can be delivered at different times and in proper sequence relative to one another.

Figure 10:
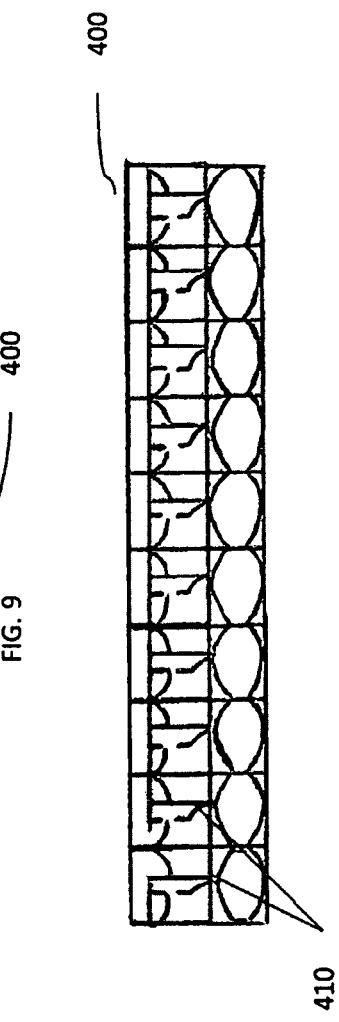
FIG. 10 is side cross-sectional view of an array of micro/nano barbed implants.

It will be appreciated that the drug delivery devices 410 can be one of the systems previously described herein. For example, the drug delivery devices 410 can be of a lancet structure (FIGS. 1-4) or a barbed implant structure (FIG. 5-7). FIG. 10 shows the array being formed of a lancet structure.

Figure 11:
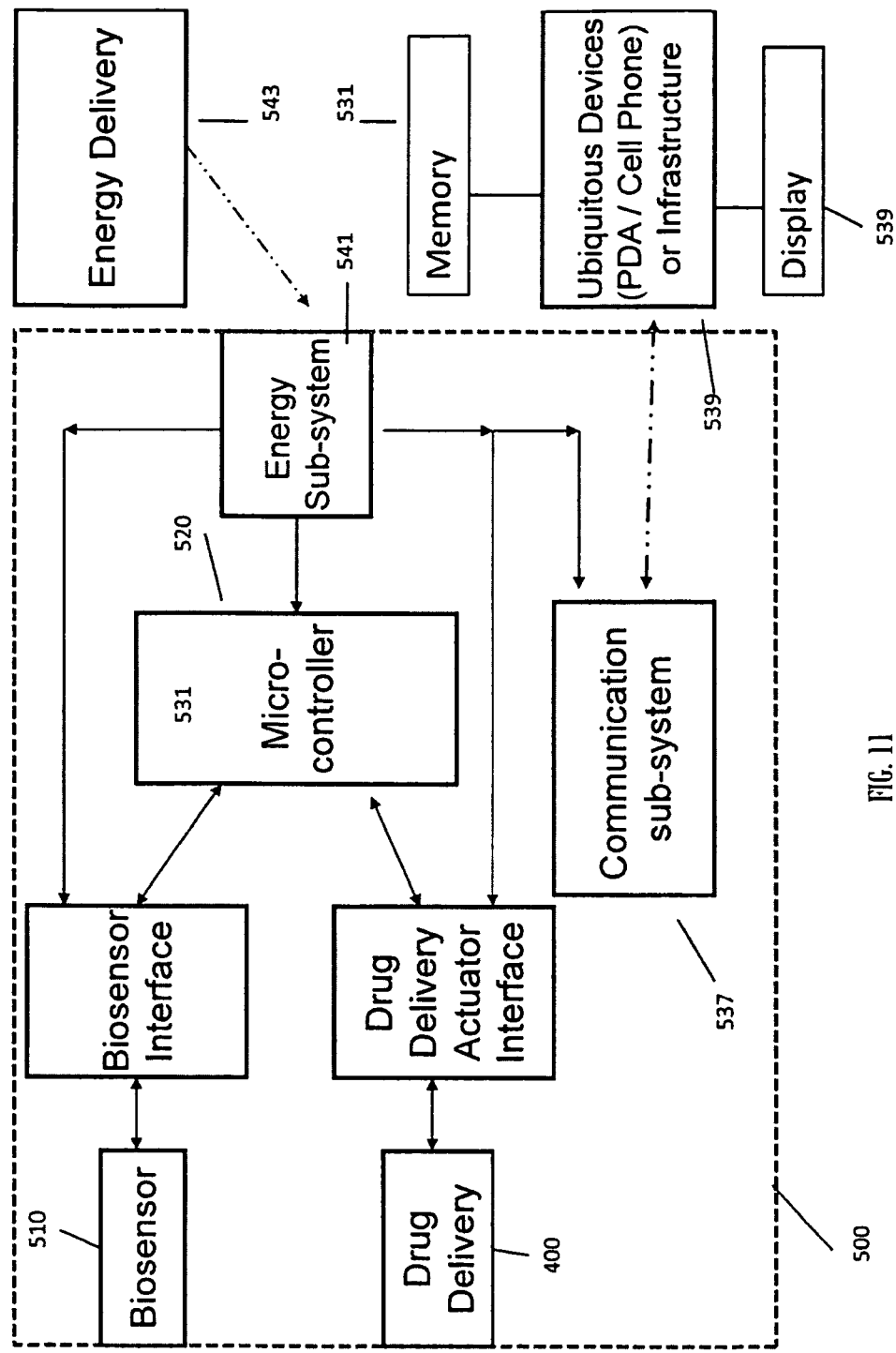
FIG. 11 is schematic diagram of a biofeedback system.

In yet another embodiment illustrated in FIG. 11, any of the previous embodiments, including the array 400 can be linked to a biofeedback system 500 that includes a microprocessor, a programmable input, etc. to control delivery of the drug(s) in the array 400. The biofeedback system 500 includes at least one sensor 510 that is in communication with the biofeedback system 500. During biofeedback, special sensors 510 are placed on or in the body and may be incorporated in the lancet structure 130 or the holding post 216. These sensors 510 measure the clinically relevant materials that may be used to detect, diagnosis, monitor or demonstrate control over bodily function or surrogates thereof that is causing the patient's problem symptoms, such as heart rate, blood pressure, muscle tension (EMS or electromyographic feedback), brain waves (EEC or electroencophalographic feedback), respiration, and body temperature (thermal feedback), etc. and delivers the information to the biofeedback system 500 where it is translated and can be displayed as a visual and/or audible readout. Optionally, the biofeedback sensor can be part of the transdermal drug delivery systems 100, 200, 300, 400 that have been described hereinbefore or it can be one of the delivery systems described hereinafter.

The biofeedback system 500 is in communication with a controller 520 that is linked to each of the drug delivery devices 410 of the array 400 and is configured to actuate (energize) each of the drug delivery devices 410 at a specific point in time or to actuate only a portion of the drug delivery devices 410 rather than all of them as a function of the person's requirements relative to a target value using the biofeedback information. As described above, this allows for controlled release of drug to the patient and since it is part of a biofeedback system, the information detected by the sensors 510 is used to decide when and how to trigger release of the drug. For example, if the sensor 510 is measuring a property of the patient's blood, and the measured values fall outside of an acceptable range, the sensor 510 will send a signal to the biofeedback system 500 which in turn signals the control system 520 to actuate one or more devices 410 that contain the specific drug(s) that is to be administered to correct and combat the detected condition. The information from the biofeedback system 500 may also be sent to the control system 520 where it may be stored in memory 531 and/or displayed 530 or transmitted for display immediately or in an appropriate time and manner to patient and or others, including physicians and/or mange care organizations, to demonstrate effectiveness and or progress of therapy. Memory 531 can be internal memory that is associated with the master controller 520 or it can external memory that is located remote from the inter-dermal delivery device and is accessed using the communication network described below.

A communication subsystem 537 is provided for communicating information from the controller 520 to another device, such as an external device (e.g., handheld unit or a computer that is connected over a network to the communication subsystem 537). The means for sending information (communication subsystem 537) can include use of a radio frequency transmitter or other appropriate mechanism.

An external device 539 (ubiquitous device) is in communication with the subsystem 537 to allow information and control signals to flow between the intra-dermal device (e.g., the subsystem 537 thereof) and the external device 539. The external device 539 thus includes a receiver which can be incorporated or may be a standalone device such as a handheld device, e.g., a cellular phone, a Personal Digital Assistant (PDA), a media player (e.g., an I-POD) or similar electronic device that contains its own energy source, a CPU, and interface software. In other words, the means for sending information can be provided in a handheld unit that has a receiver and it can be provided either be a unit that is dedicated to performing the function described herein or it can be supplied as part of and a feature of another device, such as a cellular phone. Alternatively the receiver 539 may be a part of common communication infrastructure services, such as WiFi, WiMax, cellular communication towers, etc. It will be understood that the interface should include signal transmission that is appropriate to Health Maintenance Organizations, Insurance Companies, and or Managed Care companies, as well as patients and physicians already described. In this manner, information can be readily transmitted from the intra-dermal delivery device to a person at a remote location via the use of external communications devices. A physician or the like can thus monitor, over an external device 539, the measurements (bio-properties) taken at the intra-dermal delivery device and since the external device 539 communicates with the intra-dermal delivery device, the physician can send control signals to the controller 520 to cause immediate release of drug or the like.

Once again, it will be understood that the present device has both macro and micro/nano sized features and in particular, the features (e.g., microneedles, barbs, etc. as disclosed herein) that are moved into the intra-dermal space are micro/nano sized, while the structure (e.g., a patch or casing as disclosed herein) that supports these are on a macro-scale since this placed on the user's skin.

A power source or energy subsystem 541, such as a battery, is provided for powering the microcontroller 520 and any other electronic components that may need powering. A charger or other means for energy delivery 543 for charging power source 541 or otherwise powering the energy subsystem 541 is provided.

It will also be appreciated that the array of drug delivery devices 410 can be part of a cartridge-based delivery system in which an applicator is used. The applicator includes a compartment that removably receives the array cartridge and properly positions the drug delivery devices 410 relative to the electronics of the applicator. The electronics, including a controller, communication subsystem(s) and the energy subsystems, can be part of a permanent interface device that is adjacent the compartment that receives the cartridge (as by inserting the cartridge through a slot). The user thus simply inserts the cartridge into the applicator and this results in proper alignment with the firing mechanism that causes the implants to be selectively and controllably delivered to the patient since the controller of the applicator (microprocessor) can be programmed depending upon the patient's needs to sequentially fire a prescribed number of the drug delivery devices 410 over a period of time to delivery the drug at set time intervals and over the period of time. The patient can simply insert a fresh array cartridge once a day/week/month, etc.

FIG. 12 illustrates a transdermal delivery system 600 according to yet another embodiment. The system 600 includes a micro/nano removable barb assembly 610 and a protective gel layer 620. In particular, the assembly 610 includes a plurality of barbs 612 (can be arranged as an array) that extend from a flexible substrate 614 and contain a sharp, pointed end 616. The barbs 612 protrude from the substrate 614 and can be oriented perpendicular thereto. The protective gel layer 620 is disposed opposite the substrate 614 in that the protective gel layer 620 is located along the pointed ends 616 of the barbs 612.

The barb configuration operates in the same manner as the barb configurations described above in that the drug to be delivered is incorporated into the barb (implant) structure. However, in this embodiment, the implant force comes from manually applying pressure to the top surface of the flexible substrate 614 or via pressure applied by an applicator. The protective gel layer 620 provides: a stable protective environment for the micro/nano structures; a pleasant skin contact surface and potentially the ability to incorporate a local anesthetic agent/antimicrobial agent to provide a benefit during barb insertion.

When a force is applied to the top plane of the flexible substrate 614, the micro/nano sized barb structures 612 penetrate through the protective gel layer 620 and pierce/enter the skin to the desired depth. The dimensions of the barbs 612 are thus selected so that the barbs 612 are delivered to the desired location underneath the patient's skin. Once the force being applied to the substrate 614 is removed, the barbs 612 disengage from the holding posts 216 and remain in the desired location for dissolution/disintegration/resorption per application design for a given treatment.

The flexible substrate 614 can be formed of any number of different materials and can have any number of different constructions. For example, the flexible substrate 614 can be form of a pliable material that can be comprised of a plurality of functional layers, including an chemically "inert" barb protective layer, an anesthetic layer and an adhesive layer, where the layers may be separate an distinct from each other or where they may be formulated in combination. The skin contact layer including a topical anesthetic, which may be from but not limited to (benzocaine, butamben, dibucaine, lidocaine, oxybuprocaine, pramoxine, proparacaine (Alcaine), proxymetacaine, and tetracaine (AKA amethocaine). The anesthetic is incorporated in a gel layer which may be comprised of cross-linked polymers or other materials, preferably something inert such as silica. The gel layer may have adhesion properties to ensure proper surface to skin contact and also allow for pain free removal as required.

This type of system 600 can be used for drug or cosmetic applications.

FIG. 13 illustrates an applicator 700 that can be used in combination with the system 600. The applicator 700 has a body 710 that contains an interior compartment 720 that includes a first supply section 722 and a second section 724. The interior compartment 720 stores a feedstock of drug delivery devices that contain the drug(s) to be delivered. For example, a roll of the micro/nano removable barb assembly 610 and protective gel layer 620 can be disposed about a spindle or gear 726 that permits unwinding of the barb/gel assembly. The body 710 can include one or more guide members 730 that serve to route the barb/gel assembly through the interior compartment 720 as it is unwound.

Along one surface 712 of the body 710, an applicator window 730 is formed for delivering the drug containing structures (barb/gel) to the patient. The roll of barbs/gel is routed so that it passes adjacent the window 730 such that the gel layer 620 faces the window and the pointed ends of the barbs face the window 730 to permit them to be implanted into the patient. To implant the barbs 612 into the patient, the applicator can be actuated to cause a force to be applied to the substrate 614 to cause the barbs 612 to be advanced through the window 730 and into the patient's skin as described above.

After implanting a predetermined number of barbs 612 (e.g., the ones visible through the window 730), the applicator 700 is manipulated to cause the roll to be advanced and the spent micro/nano barbs 612 are taken up on a spindle or gear 740. For example, the applicator 700 can include a knob that causes advancement of the feedstock of barbs when it is rotated. Other mechanism can equally be used. The barbs 612 and gel layer 620 can be routed in the body 710 such that it is fed to the window 730 in a manner that causes the barbs 612 and gel layer 620 to protrude beyond the surface 712 and thus when the applicator 700 is pressed against the skin to position surface 712, into contact with the skin, the barbs 612 are implanted. Alternatively, the applicator can have some type of firing mechanism that applies a force to the substrate 614 to cause the barbs 612 to be implanted.

It will also be appreciated that the roll of the micro/nano removable barb assembly 610 and protective gel layer 620 can be part of a cartridge and thus, the applicator 700 can be a cartridge based system. Electronics, including controllers, etc., of the applicator 700 are located on a more permanent interface device. The patient simply inserts a fresh array cartridge once a day/week/month, etc.

Example

One application for a drug delivery system is the human ear. More specifically, the barbed implant design of FIGS. 5-7 can be configured as an anti-infective implant formulation for use prophylactically or as a curative agent in middle ear infections. The barbed implants are coupled to a topical application (e.g., similar to a swab (Qtip) or a film) and the barbed-based formulation is applied to the outer surface of the eardrum allowing the micro/nano barbs to penetrate the membrane and enter the region of the middle ear where the barbs with anti-infective agents (antibiotics) are deposited to pre-condition or treat an already infected ear space. The applicator may take the form of a gel, or multi-layer film which could include a topical anesthetic to facilitate application to areas where nerves have been sensitized.

Example

Another example is for the barbed implant design of FIGS. 5-7 can be configured as an anti-infective or anti-allergic implant formulation for use prophylactically or as a curative agent in nasal infections or rhinitis. The barbed implants are coupled to a topical application (e.g., similar to a swab (Qtip) or a film, or spray) and the barbed-based formulation is applied to the nasal mucosa allowing the micro/nano barbs to penetrate the membrane and enter the region of the middle ear where the barbs with anti-infective agents (antibiotics), anti-allergic agents (anti-histamines, etc.) are deposited to pre-condition or treat an already effected nasal space. The applicator may take the form of a gel, spray or multi-layer film which could include a topical anesthetic to facilitate application to areas where nerves have been sensitized.

Example

Another application is for a tumor/organ wrap that is configured to directly infuse sustained release agents. The wrap is formed of a "fabric" or shrinking polymer skin to drive "barb" open portals and allow for active transfer of agent to the target tissue. The wrap can be applied laproscopically by spray or roll on.

In yet another embodiment, the transdermal delivery systems disclosed above can be part of a system that provides a visual indicator to the person using the system that the application of drug was or was not successful. For example, the applicator and the barbs can be constructed so that a color change occurs on release (implant) of the barb into the patient's skin, thereby providing a visual indicator or confirmation that a successful delivery resulted. In other words, when the barbs are removed from the holding posts or other supporting structure, a color change results. This could occur by having the distal tip of the holding post be formed of a material that upon discharge of the surrounding barbed implant and upon exposure to air, changes color. Alternatively, the end of the holding post may have a color that is initially covered up by the barbed implant but upon implanting the barbed implant into the patient, the color is exposed.

The user of such a system will thus be able to readily determine how many barbed implants were successfully delivered into the patient. For example, when the barbed implant are located at the end of a swab, after the swab is pressed against the patient's skin, it will readily be apparent what areas of the swab successfully delivered their barbed implants by simply looking at the surface of the swab. The user will see regions of no color (or a first color) indicated implants still intact and regions of another color indicated successful implantation.

Yet another delivery system application includes systems as described hereinabove in which a substance is delivered locally and below the stratum corneum and has a composition that swells after implantation so as to apply pressure to the stratum corneum from below the surface. One application of such a topical application is to reduce the appearance of wrinkles or to tighten the surface of skin.

For example, the barbed implant disclosed herein can be part of a cosmetic wrinkle reduction system. The system enables anyone desiring to reduce or temporarily eliminate facial wrinkles (around the mouth, nose, eyes, etc.) typically associated with aging by easily and painlessly implanting an appropriate amount of swelling barbed implants between the stratum corneum and the stratum germinativum where interstitial fluids will cause the barbs to expand and apply appropriate pressures to the stratum corneum to fill in the valleys that cause wrinkles. The barbed implants may be formed from materials that are endogenous in the body and that can be complexed to form swelling hydro-gel type matrix. As with the other embodiments, the barbed implants will be absorbed and eliminated without potential accumulation.

Figure 14:
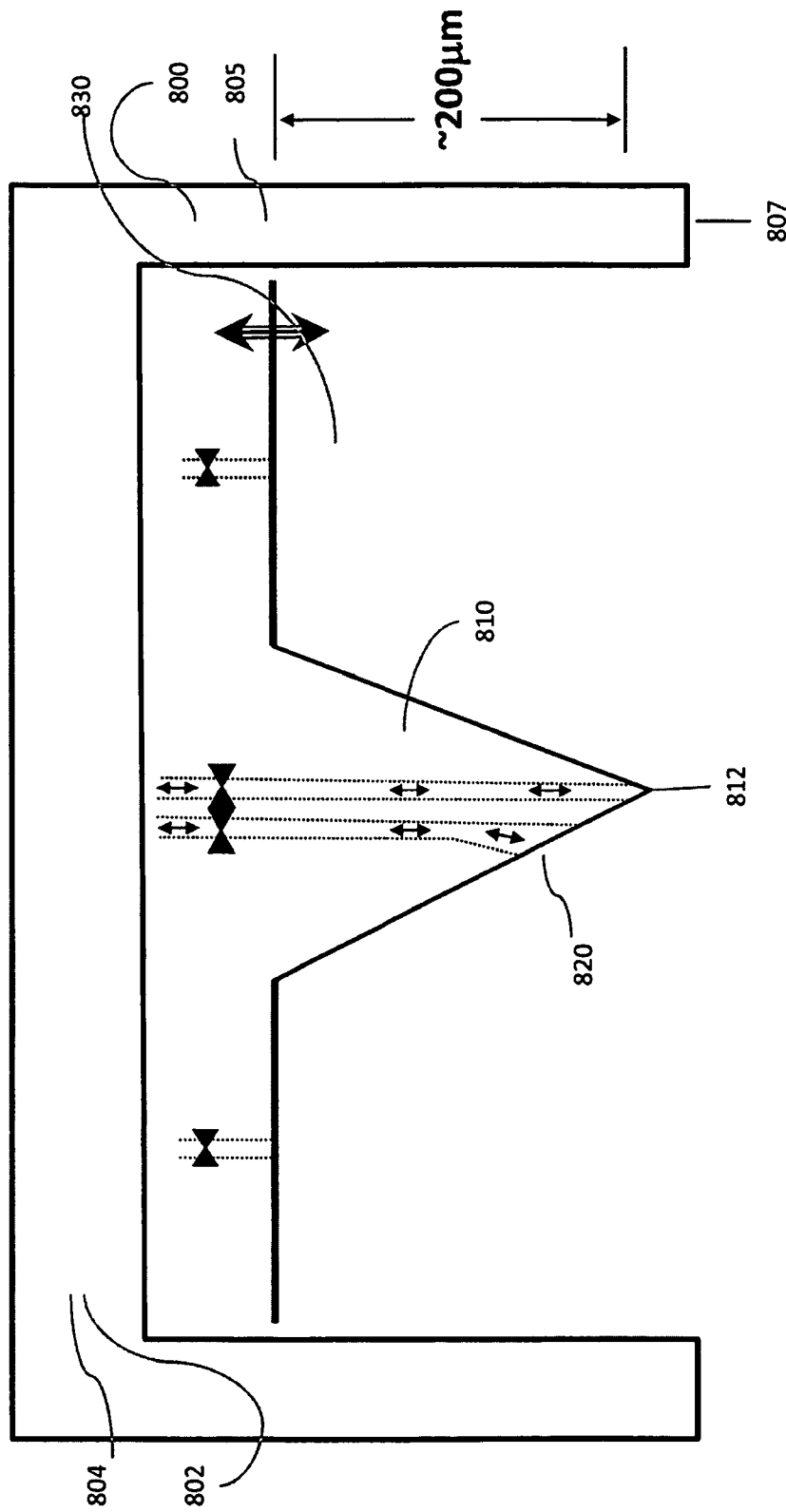
FIG. 14 is a cross-sectional view of an alternate micro/nano drug delivery device for use with the cell of FIG. 1.

Now referring to FIGS. 14-22 in which other embodiments are illustrated. In FIG. 14, a device 800 that is part of a micro/nano transdermal delivery system and includes at least one and preferably a plurality of microneedles 810 with channels 820 formed therein. The microneedle(s) is mounted on an oscillating movable base 830. The device 800 includes a fixed casing 802 that is open along a bottom 804 thereof. In the illustrated embodiment, the fixed casing 802 has a top portion 804 that closes off the fixed casing 802. The movable base 830 is located proximate the top portion 804 and extends across side walls 805 of the casing 802.

The contact between a surface of the device (e.g., a bottom surface 807) and the skin is managed by and at the same time limited by the fixed casing 802. The microneedles 810 are oscillated at a frequency between about 0 kHz to about 3 MHz (preferably between about 5 kHz to about 2 MHz), with amplitudes of between about 0 to about 1000 microns (preferably between about 5 microns to about 250 microns) as a result of the base 830 being movable. Amplitudes of oscillations are varied for drilling/opening channels in the stratum corneum/epidermis/dermis and/or pumping/suction of drug/blood/interstitial fluids. The oscillating microneedles 810 (with respect to the fixed device casing 802) create holes with specified properties in the stratum corneum. The design of the microneedles 810 varies for specific requirements and depending upon the particular application. The creation of the back pressure and/or the interface pressure between the stratum corneum and the device 800 interface pressure drive the drug to the target level in the intra-dermal space.

Figure 15:
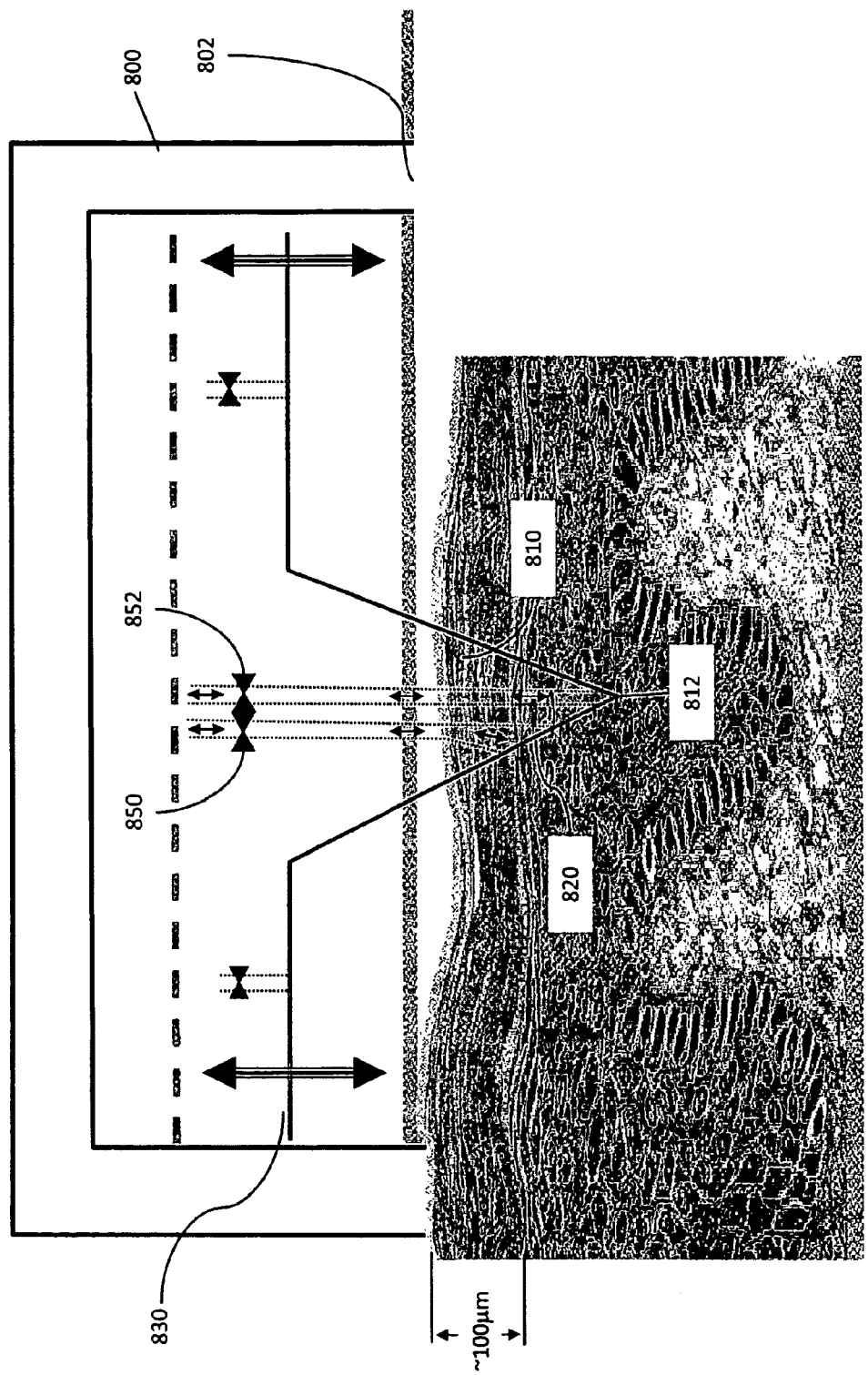
FIG. 15 is a cross-sectional view of an alternate micro/nano drug delivery device according to another embodiment.

FIG. 14 shows a basic device 800 for both delivery of a drug and extraction of a fluid, such as blood and/or interstitial fluid. FIG. 14 shows the device 800 in a normal rest position where the microneedles 810 are not extended into an out-of plane delivery or extraction position. FIG. 15 shows the device 800 in an activated condition where the base 830 has oscillated relative to its position in FIG. 14 and this results in the microneedles 810 being moved out of the plane such that the distal tips 812 of the microneedles 810 extend below the bottom surface 807 of the device 800 (casing 802). FIGS. 14 and 15 show two channels 820 being formed therein. The channels 820 can have the same construction or they can contain different constructions as shown. FIG. 15 thus shows an out-of-plane oscillation where the distal tip 812 advances into the skin to the desired depth as described herein.

In FIG. 15, each of the channels 820 includes a flow control device 850, 852 (such as directional valves/pumps) that are included in the respective channels 820 to control flow within the channel 820 to be controlled. The flow control component 850, 852 is in communication with the master controller/processor of the device 800 to allow control thereof depending upon the precise application and state of the microneedle 810. Additional flow control devices can be provided in the device in locations remote from the actual channels to control flow of fluid within the device.

Figure 16:
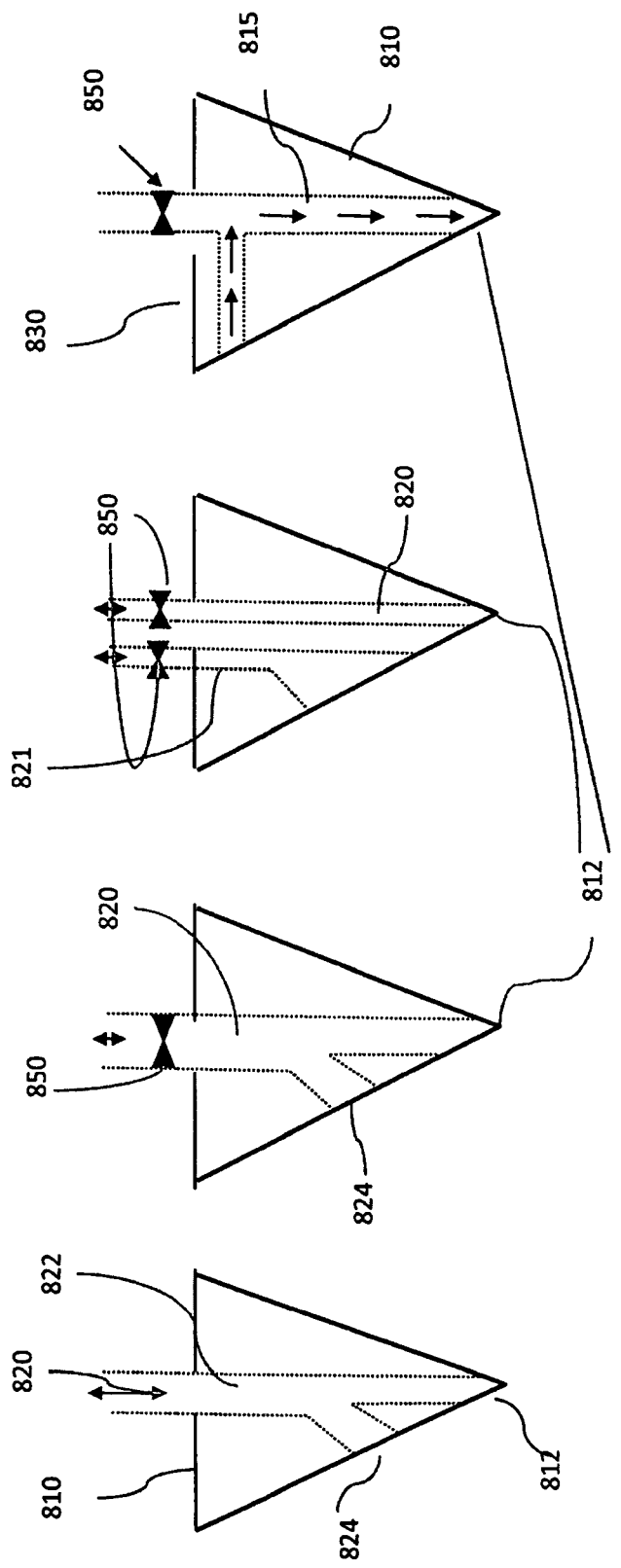
FIG. 16 is a cross-sectional view of an alternate micro/nano needle according to another embodiment.

FIG. 16 shows a device 900 that includes a number of different types of microneedle constructions and in particular, channel constructions. It will be understood that the device 900 that is shown can include one type of microneedle construction or it can include a combination of different types of microneedle constructions. For example, FIG. 16A shows a microneedle 810 that has a passive free-flow channel construction. In particular, the microneedle 810 includes a single channel 820 that has a main section 822 that is open at the top and bottom of the microneedle 810 and includes a side or secondary section 824 that is open along the side of the microneedle 810 prior to the distal tip 812. Fluid flows freely in both directions within the channels. FIG. 16B shows a microneedle 810 of a different construction where there is a single channel 820 with flow control. In particular, the single channel 820 is similar to the channel shown in FIG. 16A in the channel 820 that has a main section 822 that is open at the top and bottom of the microneedle 810 and includes a side or secondary section 824 that is open along the side of the microneedle 810 prior to the distal tip 812. At or near the top end of the main section 822, a directional valve/pump 850 is included to control flow within the channel 820 to be controlled. The flow control component 850 is in communication with the master controller/processor of the device 800 to allow control thereof depending upon the precise application and state of the microneedle 810.

FIG. 16C shows a microneedle 810 that is similar to those in FIGS. 16A and 16B; however, in this embodiment, the microneedle 810 has a multi-channel construction. More specifically, the microneedle 810 includes a first channel 820 and second channel 821. The first channel 820 is open at the top end and is open at the distal end. The second channel 821 is open at the top end and opens along the side of the microneedle 810. At or near the top end of both the first section 820 and the second channel 821, directional valves/pumps 850, 852 are included in the respective channels to control flow within the channel 820, 821 to be controlled. The flow control component 850 is in communication with the master controller/processor of the device 800 to allow control thereof depending upon the precise application and state of the microneedle 810.

FIG. 16D shows a microneedle 810 that includes a back pressure channel. More specifically, the microneedle 810 includes a main channel 815 that has a top end and a bottom end that is open at the distal end of the microneedle 810. A side or back channel 831 is provided in the microneedle 810 such that one end of the side channel 831 is open along the side of the microneedle 810 and the other end communicates with the main channel 815. At a location above the juncture between the side channel 831 and the main channel 815, a directional valve/pump 850 is included in the respective channels to control flow within the channel to be controlled. The flow control component 850 is in communication with the master controller/processor of the device 800 to allow control thereof depending upon the precise application and state of the microneedle 810. The arrows shown in FIG. 16D reflect fluid flow.

Figure 17:
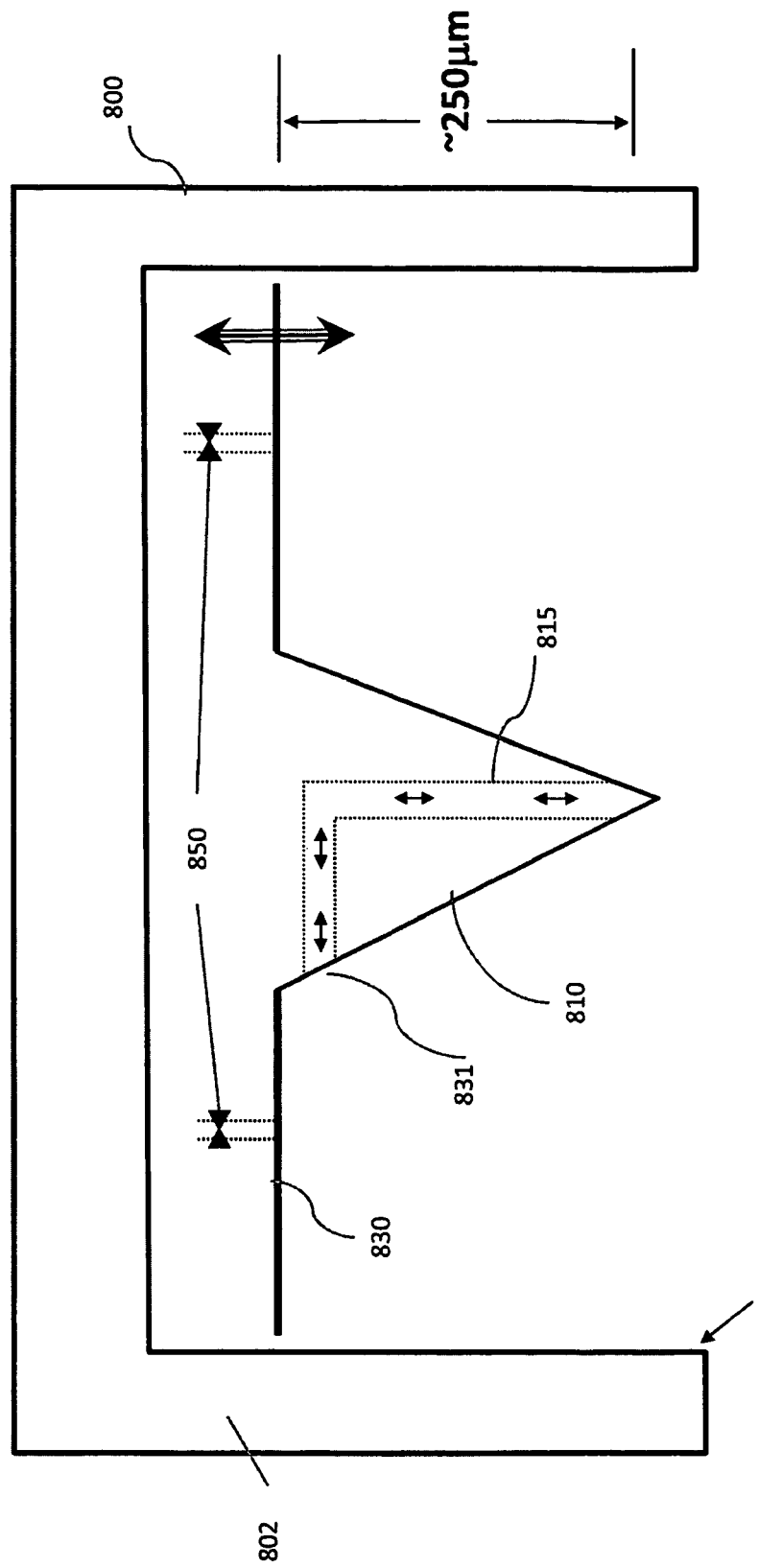
FIG. 17 is a cross-sectional view of an alternate micro/nano drug delivery device according to another embodiment.
Figure 18:
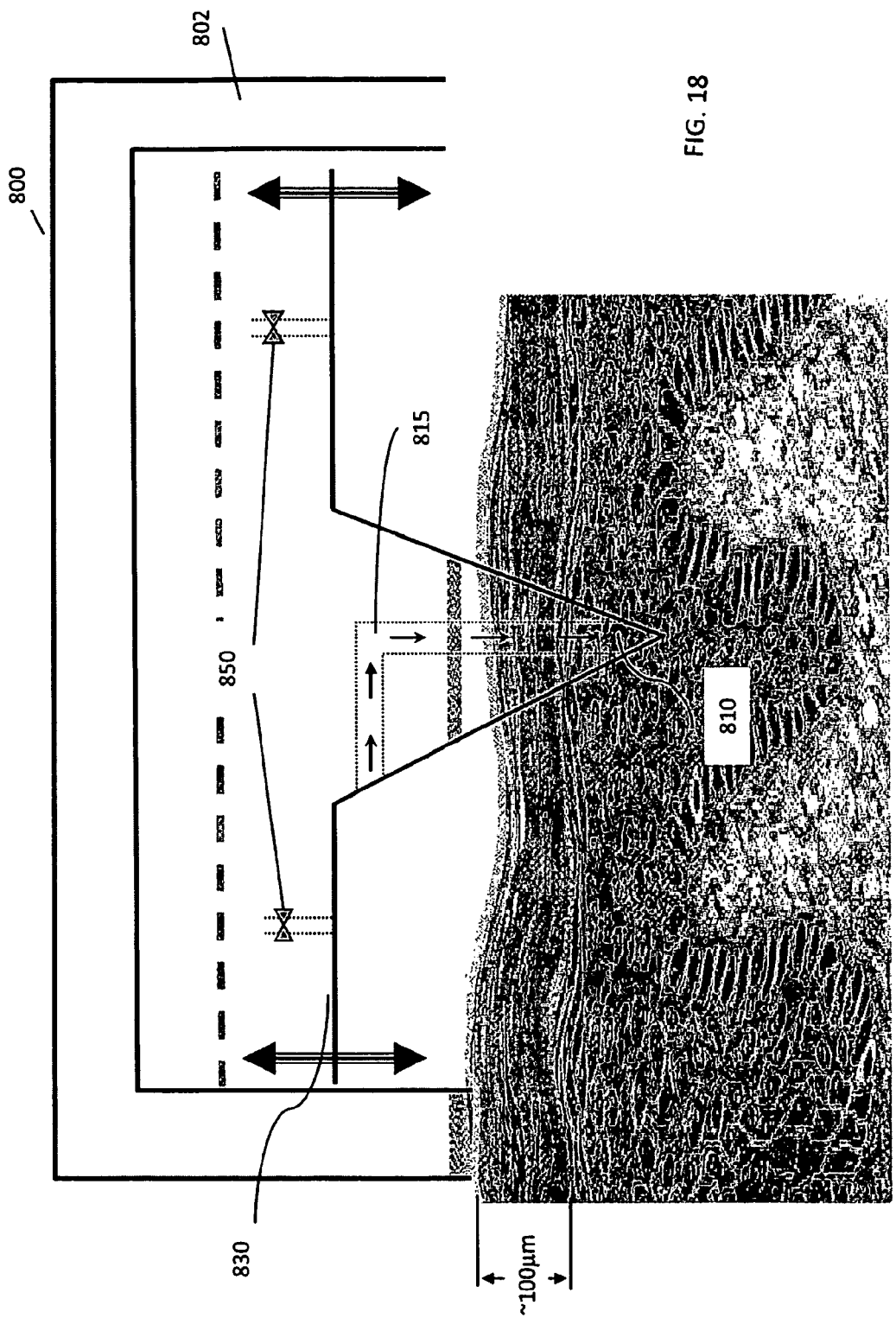
FIG. 18 is a cross-sectional view of an alternate micro/nano drug delivery device depicting oscillatory movement and associated pressure differential according to another embodiment.

FIG. 17 shows the backpressure microneedle embodiment of FIG. 16D installed in a device for use in a micro/nano transdermal delivery system. In FIG. 18, there are two flow control components 850 that allow control over the fluid as it flows within the device, such as when the drug to be delivered flows into the microneedle 810. In FIG. 17, the microneedle 810 is in a normal, rest position where the distal tip of the microneedle 810 does not extend beyond the bottom of the device (casing). FIG. 18 shows the microneedle 810 in an actuated state (oscillated out-of-plane) where the microneedle 810 extends beyond the casing resulting in the distal tip of the microneedle 810 being driven into the skin.

FIG. 19 shows a sub-unit 1000 constructed in accordance with the present invention. The unit 1000 includes a body 1010 that has a drug containing reservoir 1020 that is contained between a pair of substrates or layers 1022. The layers 1022 can be in the form of an actuator that is configured to selectively fire one or more microneedles 810. For example, the layers 1022 can be formed of piezoelectric strips that, as is known, change shape when powered by small amounts of electricity. The layers 1022 can be other types of actuators, such as a pressure actuator and/or motion actuator, which under select conditions, causes deformation of the unit 1000 in a manner described below resulting in controlled release of the drug contained in the reservoir 1020.

The unit 1000 includes at least one and preferably a plurality of microneedles 810 that are in selective communication with the reservoir 1020. The precise structure and interface between the reservoir 1020 and the microneedles 810 can vary depending upon the particular application and other considerations. For example, there can be a main channel 1030 that is in selective communication with the reservoir since a valve/pump 1040 is provided within or at the end of the main channel 1030 to control flow of the drug from the reservoir 1020. The main channel 1030 is also in communication with an internal channel network that delivers the fluid from the reservoir to a number of channels that directly feed the microneedles 810 and allow the drug to be discharged through the distal tips of the microneedles 810.

The unit 1000 further includes biofeedback system 500 that is in communication with a controller 520 that is linked to each of the drug delivery devices (microneedles 810 in this case) of the array and is configured to actuate (energize) each of the microneedles 810 at a specific point in time or to actuate only a portion of the microneedles 810 rather than all of them as a function of the person's requirements relative to a target value using the biofeedback information. As described above, this allows for controlled release of drug to the patient and since it is part of a biofeedback system, information detected by the sensors 510 is used to decide when and how to trigger release of the drug. For example, if the sensor 510 is measuring a property of the patient's blood, and the measured values fall outside of an acceptable range, the sensor 510 will send a signal to the biofeedback system 500 which in turn signals the control system 520 to actuate one or more microneedles 810 that contain the specific drug(s) that is to be administered to correct and combat the detected condition.

The information from the biofeedback system 500 may also be sent to the control system where it may be stored and or displayed 530 or transmitted for display immediately or in an appropriate time and manner to patient and or others, including physicians, to demonstrate effectiveness and or progress of therapy. The means for sending information may include use of radio frequency transmitter or other appropriate mechanism, generally shown as communication subsystem 505 in FIG. 19. As previously mentioned, the receiver can be incorporated or may be a standalone device such as a handheld device, e.g., a cellular phone, a Personal Digital Assistant (PDA), a media player (e.g., an I-POD) or similar electronic device that contains its own energy source, a CPU, and interface software. In other words, the means for sending information can be provided in a handheld unit that has a receiver and it can be provided either be a unit that is dedicated to performing the function described herein or it can be supplied as part of and a feature of another device, such as a cellular phone. Alternatively the receiver may be a part of common communication infrastructure services, such as WiFi, WiMax, cellular communication towers, etc. It will be understood that the interface should include signal transmission that is appropriate to Health Maintenance Organizations, Insurance Companies, and or Managed Care companies, as well as patients and physicians already described.

It will also be appreciated that the biofeedback system 500 disclosed herein is not limited to being used as a part of a larger drug delivery device or in combination therewith. Instead, all of the drug delivery devices disclosed herein can be modified so as to not include the drug delivery component (e.g., reservoir) or if this component is present, the communication from the feedback system 400 to the control system can be for diagnostic purposes only and not related to signals or instructions relating to release of drug. In other words, the biofeedback system can communicate with the control system which can store and/or display the received information irrespective of drug delivery.

Now referring to FIG. 20 in which another sub-unit 1100 is shown. The sub-unit 1100 includes the fixed casing 802 that houses the drug containing reservoir 110, the microneedles 810 and the other components. In the illustrated embodiment, the reservoir 110 is in communication with at least one actuator. For example, one or more pressure actuators 1110 can be provided for applying a select force to a local area of the unit. In the illustrated embodiment, the pressure actuators 1110 are located along the top of the reservoir 110. In addition, one or more motion actuators 1120 can be provided and in the illustrated embodiment, a plurality of motion actuators 1120 are located along the bottom of the reservoir 110 and are spaced apart from one another. The motion actuators 1120 are located so as not to obstruct the flow of the drug from the reservoir 110 into the top of the main channel 821 in the microneedle 810. The combination of these actuators provides a means for actuating select microneedles 810 to cause advancement ("firing") of the microneedle 810 into the skin of the patient and to permit the microneedles to resume their normal retracted, rest positions.

As with the other embodiments, one or more valves/pumps 1130 can be provided for controlling the flow of fluid within the device. For example, one valve/pump 1130 can be provided in a line that communicates between the reservoir 110 and sensor 510 and one or more valves/pumps 1130 can be provided between the reservoir 110 and the channel architecture. As with other embodiments, the microneedles 810 can be extended beyond the casing and into the skin.

FIG. 21 shows another sub-unit 1200. This embodiment is similar to the other embodiments; however, in this embodiment, there are piezoelectric strips 1210 located along both the top and bottom of the reservoir 110. The strips 1210 thus define the interior of the reservoir 110. Actuation of the piezoelectric strips 1210 causes selective firing (deformation) of certain microneedles 810.

FIG. 22 discloses an alternate micro/nano drug delivery device 1300 depicting biosensor interface with drug delivery sub-unit and control system.

The device 1300 includes the sub-unit 1200 shown in FIG. 21 and further includes biofeedback system 500 that is in communication with a controller 520 that is linked to each of the drug delivery devices (microneedles 810 in this case) of the array and is configured to actuate (energize) each of the microneedles 810 at a specific point in time or to actuate only a portion of the microneedles 810 rather than all of them as a function of the person's requirements relative to a target value using the biofeedback information. As described above, this allows for controlled release of drug to the patient and since it is part of a biofeedback system, information detected by the sensors 510 is used to decide when and how to trigger release of the drug. For example, if the sensor 510 is measuring a property of the patient's blood, and the measured values fall outside of an acceptable range, the sensor 510 will send a signal to the biofeedback system 500 which in turn signals the control system 520 to actuate one or more microneedles 810 that contain the specific drug(s) that is to be administered to correct and combat the detected condition.

In the illustrated embodiment, the sensor 510 is disposed proximate (adjacent) a reservoir 511 that is in selective communication with the reservoir 110 via a conduit or passage 111. A pump/valve 850 is disposed along the conduit 111 to permit flow between the reservoirs 511, 110. Other pumps/valves 850 are disposed in communication with the microneedle channels to selectively allow fluid to flow between reservoir 110 and the microneedles 810. A pressure actuator 1310 is provided and is located in reservoir 511 that is adjacent the sensor 510.

As shown in FIG. 22, the electronic controller 520 is in communication with the working components of the device including the pumps/valves 850, sensor 510, pressure actuator 1310, etc.

The information from the biofeedback system 500 may also be sent to the control system where it may be stored and or displayed or transmitted for display immediately or in an appropriate time and manner to patient and or others, including physicians, to demonstrate effectiveness and or progress of therapy. The means for sending information may include use of radio frequency transmitter or other appropriate mechanism. As previously mentioned, the receiver can be incorporated or may be a standalone device such as a handheld device.

The devices of FIGS. 14-22 are configured to perform any number of different operations. For example, in one embodiment, a negative back pressure (difference) is utilized to extract blood and/or interstitial fluid from the intra-dermal region into the appropriate reservoir(s) (e.g., 511 in FIG. 22) and in contact with a sensor(s) 510. Pressure oscillations and motion control (e.g., using the disclosed actuators, piezoelectric strips, etc.) are utilized to move fluid in and out of the reservoir 511 and in and out of contact with the sensor(s) 510. The pressurized reservoirs utilize a synchronization scheme. Frequency and duty cycles as well as synchronization are optimized for the maximum performance. The biological sample can be obtained using any number of different techniques as described hereinbefore.

Biosensing of the biological material can be accomplished utilizing electrical/electrochemical/mass detection. The system can utilize one or more of i) application of DC voltage and measuring the DC current response (amperometry), ii) application of a DC current and measuring the DC voltage response (potentiometry), or iii) application of an AC voltage and measuring the AC current response (capacitance or impedance). In all cases, three electrodes are incorporated into the intra-dermal delivery, diagnostic and communication device, the working, reference and counter electrodes. These electrodes are positioned as closely together as possible, with analyte detection occurring at the working electrode. Ideally, the electrodes are designed such that the voltage is applied between the working and reference electrodes, while current is detected through the counter electrode. Mass deposition on a functionalized surface can be detected by inertia based methods such as the resonance frequency shift of a cantilever beam due to its change of mass.

Example

The following is a general description of how one of the devices of FIGS. 14-22 can be used as a drug delivery application. In a first step, the back pressure is increased or the back pressure is oscillated out-of-phase with the microneedle motion. This results in the stratum corneum being pecked for a duty cycle (defined by a frequency, amplitude, and duration) and the creation of multiple holes in the stratum corneum. Large drug molecules are forced through the stratum corneum due to the (oscillating) back-pressure motion. In a subsequent step, the "pecking motions" are stopped and the (static) back-pressure is kept until the holes in stratum corneum are closed/healed.

In accordance with one embodiment, a mode of operation diagnostic includes decreasing the back-pressure (or oscillate the back pressure out-of-phase with the needle motion); peck the stratum corneum for a duty cycle (frequency, amplitude, and duration; thereby creating multiple holes in the stratum corneum. This forces blood/fluid from these holes thorough the stratum corneum due to the (oscillating) negative back-pressure into the sensor(s) reservoir(s) that contains the drug.

The pecking motions are stopped and the back-pressure is increased to the internal body pressure until the holes in stratum corneum are closed/healed. There are a number of advantages that can be realized with the device and method of the present invention, including but not limited to the following: the required contact time with the top of the stratum corneum is very short (micro-seconds since the operation time-scale is short (kHz-MHz)); no need for long contact periods with the top of the stratum corneum since the device can be activated as the contact is established; only a brief period of contact with the stratum corneum is required (i.e., microseconds); large molecules can be delivered through "large holes" in the stratum corneum (due to the microneedle size); multi-drug delivery is possible due to modular design of reservoirs/sensors and rapid operations; provides time for the stratum corneum to heal due to micro-second operations and hours of usage (off) times; it is minimally invasive; rapid blood/fluids extraction leading to multiply tests/monitors; large number of control parameters (amplitude, frequency, duration, etc.) provides flexibility in device design, operations, and uses; very rapid dosage alterations on-the-fly (as needed) are possible due to short operation times; can be programmed for continuous, patterned, on-demand or feedback-controlled drug delivery/monitoring; novel microneedle designs can be integrated and this provides further flexibility in delivery design and utilization regimes; active process control is possible due to the large number of control parameters; short operation times minimize energy consumption; modular design allows the dispersion of chemical permeation enhancer and the integration of thermal/ultrasonic/electrical enhancing components.

It will be understood that the components, including the sensors and drug delivery devices, shown in FIGS. 14-22 are suitable for use in the system generally illustrated in FIG. 11.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:
1. An intra-dermal delivery system comprising:
at least one micro/nano sized drug delivery device for intra-dermally delivering a drug below the stratum corneum, the drug being stored in a reservoir within the device, the device having an actuator for causing selective movement of at least a portion of the device to deliver the drug below the stratum corneum, wherein the drug delivery device includes:
a fixed casing having a top wall and side walls that define a hollow interior, the casing having a completely open bottom between the side walls such that bottom edges of the side walls are for placement against the patient's skin;
an oscillating base disposed within the hollow interior of the casing such that the oscillating base extends between the side walls of the casing, the base oscillating relative to the fixed casing, wherein the oscillating base has at least one microneedle that is integral thereto and extends outwardly from a bottom surface of the base whereby the microneedle oscillates a sufficient distance as part of the oscillating base to cause the microneedle to contact and penetrate the stratum corneum;
a programmable controller in communication with the at least one device for controlling the actuation of the actuator; and
a biofeedback device that is in communication with the programmable controller and includes at least one biosensor that measures at least one bio-property of the patient,
wherein the controller is programmed based on a patient's needs to deliver the drug at a prescribed time or based on a signal received from the biofeedback device;
wherein the casing is constructed such that there is unobstructed access to the microneedle along the open bottom of the casing;
wherein the reservoir is in fluid communication with a first channel formed in the base at a location that is remote and spaced from the microneedle and selectively opens to an empty space in the hollow interior of the casing that surrounds a beveled side wall of the microneedle for receiving the drug from the reservoir, wherein the empty space is open along a bottom thereof and is configured such that the patient's skin closes off the empty space, the microneedle containing a second channel that is free of direct fluid communication with the first channel and instead is in fluid communication with the empty space that surrounds the beveled side wall of the microneedle for receiving the drug container therein, the second channel being open at a drug delivery tip of the microneedle;
wherein the actuator is operatively coupled to the oscillating base to cause controlled oscillation thereof, thereby causing the microneedle to be moved such that the drug delivery tip thereof is advanced beyond the bottom edge of the fixed casing in an extended position and into the skin below the stratum corneum, wherein in a retracted position, the drug delivery tip is located within the interior of the fixed casing above the bottom edges of the side walls so as to be spaced from the skin when the bottom edges of the fixed casing rest on the skin.

2. The system of claim 1, wherein the actuator causes the oscillating base to oscillate resulting in the microneedles oscillating at a frequency between greater than 0 kHz to about 3 MHz, with amplitudes greater than 0 microns to about 250 microns.

3. The system of claim 1, wherein the first channel is in communication with a flow control member that controls flow of the drug through the first channel to the empty space surrounding the microneedle.

4. The system of claim 3, wherein the flow control member comprises a directional valve/pump.

5. The system of claim 1, wherein the second channel is in the form of a back pressure channel.

6. The system of claim 5, wherein the back pressure channel comprises a side channel defined by the opening formed along the side surface and represents a first end of the side channel, the side channel intersecting the second channel at an opposite second end.

7. The system of claim 1, wherein there are a plurality of microneedles each of which can be actuated and moved independently from the others.

8. The system of claim 1, wherein the biosensor is in selective communication with the reservoir via the first channel that has a flow control device disposed therealong for restricting flow between the sensor and the reservoir.

9. The system of claim 1, wherein the biosensor is integrated with the body of the at least one drug delivery device.

10. The system of claim 1, wherein the biofeedback device is in wireless communication with the programmable controller.

11. The system of claim 1, wherein at least one of the biofeedback device and the biosensor measures the bio-property and sends a signal containing information regarding the measured bio-property to the programmable controller.

12. The system of claim 11, wherein the programmable controller is in communication with an external device that includes at least one of a display which can display the information regarding the measured bio-property and a memory in which the information can be stored.

13. The system of claim 12, wherein the external device is a handheld device and the communication comprises wireless communication between the handheld device and the controller.

14. The system of claim 1, wherein the actuator creates a back pressure in the microneedle causing a fluid to be drawn into the microneedle, into the empty space and into contact with the sensor.

15. The system of claim 14, wherein the fluid is one of blood and interstitial fluid.

16. An intra-dermal delivery system comprising:
at least one micro/nano sized drug delivery device for intra-dermally delivering a drug below the stratum corneum, the drug being stored in a space within the device, the device having an actuator for causing selective movement of at least a portion of the device to deliver the drug below the stratum corneum, wherein the drug delivery device includes a fixed hollow casing that is open along a bottom thereof and includes a bottom edge and one or more side walls and a movable base that has at least one microneedle that extends outwardly from a bottom surface of the base, wherein the movable base is disposed within a hollow interior of the casing and moves relative to the fixed casing such that one or more hollow spaces are formed between a side of the microneedle and the one or more side walls, the drug delivery device including a reservoir for containing the drug and one or more first channels that are in fluid communication with the reservoir and are open to the one or more hollow spaces that laterally surround the side of the microneedle, each first channel include a flow control member for controlling flow of the drug from the reservoir to the one or more hollow spaces, the at least one microneedle being in selective fluid communication with the reservoir by means of a second channel formed entirely within the microneedle and being open along a sharp distal tip of the microneedle, the second channel being also open along a surface of the side of the microneedle and in direct fluid communication with the hollow space surrounding the side of the microneedle for receiving drug that is located within the hollow space subsequent to discharge from the reservoir through the first channel, whereby the microneedle controllably moves with the base to cause the microneedle to penetrate the stratum corneum, wherein the microneedle is movable between a retracted position and an extended position, wherein in the retracted position, the distal tip of the microneedle lies above the bottom edge of the base so as to be spaced from the skin and in the extended position due to movement of the movable base, the distal tip and the opening of the second channel located thereat lie below the bottom edge of the base as a result of the distal tip being driven into the skin, whereas a degree of movement of the base is limited such that, in the extended position, the opening of the second channel formed along the side surface of the microneedle is located above the stratum corneum and is freely open to the hollow space defined between the microneedle and the one or more side walls of the casing, thereby permitting the drug to be delivered from the hollow space to the stratum corneum by flowing through the second channel as a result of a pumping action;

a programmable controller in communication with the at least one device for controlling the actuation of the actuator; and a biofeedback device that is in communication with the programmable controller and includes at least one bio-sensor that measures at least one bio-property of the patient, wherein the controller is programmed based on a patient's needs to deliver the drug at a prescribed time or based on a signal received from the biofeedback device.

17. The system of claim 16, wherein the flow control member comprises a directional valve/pump.

18. The system of claim 16, wherein the second channel is defined by a first section that is open along the surface of the side of the microneedle and a second section that extends to and is open at the distal tip and intersects the first section at a right angle.

19. The system of claim 16, wherein the movable base comprises an oscillating base that extends between the one or more side walls of the casing.

20. The system of claim 16, wherein the movable base oscillates a sufficient degree to permit the distal tip to be driven into the stratum corneum.

21. The system of claim 16, wherein the one or more hollow spaces are is open along a bottom thereof and is configured such that the patient's skin closes off the one or more hollow spaces.

22. The system of claim 16, wherein the hollow casing has a top wall that is disposed above the first channel.

23. The system of claim 16, wherein the first channel is located between the one or more side walls of the casing below the top wall.

* * * * *